(12) United States Patent
Zanella, Sr. et al.

(10) Patent No.: US 10,948,469 B2
(45) Date of Patent: Mar. 16, 2021

(54) DYNAMIC COMPARATIVE DIAGNOSTICS FOR CATALYTIC STRUCTURES AND COMBUSTIBLE GAS SENSORS INCLUDING CATALYTIC STRUCTURES

(71) Applicant: MSA TECHNOLOGY, LLC, Cranberry Township, PA (US)

(72) Inventors: Mark Flori Zanella, Sr., Chicora, PA (US); Michael Alvin Brown, Cranberry Township, PA (US); Meghan E. Swanson, Pittsburgh, PA (US); Daniel D. Santoro, Jr., Pittsburgh, PA (US); Jeff Audia, Stratham, NH (US); Ryan Alan Sherry, Cranberry Township, PA (US)

(73) Assignee: MSA TECHNOLOGY, LLC, Cranberry Township, PA (US)

( * ) Notice: Subject to any disclaimer, the term of this patent is extended or adjusted under 35 U.S.C. 154(b) by 273 days.

(21) Appl. No.: 15/597,859

(22) Filed: May 17, 2017

(65) Prior Publication Data
US 2018/0335411 A1 Nov. 22, 2018

(51) Int. Cl.
*G01N 27/16* (2006.01)
*G01N 33/00* (2006.01)

(52) U.S. Cl.
CPC ......... *G01N 33/0027* (2013.01); *G01N 27/16* (2013.01); *G01N 33/007* (2013.01)

(58) Field of Classification Search
None
See application file for complete search history.

(56) References Cited

U.S. PATENT DOCUMENTS

| 4,533,520 A | 8/1985 | Bossart |
| 4,627,269 A | 12/1986 | Forster |

(Continued)

FOREIGN PATENT DOCUMENTS

| EP | 0500598 B1 | 3/1997 |
| GB | 1550615 | 8/1979 |

(Continued)

OTHER PUBLICATIONS

Cullis, C.F., and Firth, J.G., Eds., Detection and Measurement of Hazardous Gases, Heinemann, Exeter, 29 (1981).

(Continued)

*Primary Examiner* — Paul S Hyun
(74) *Attorney, Agent, or Firm* — Bartony & Associates, LLC

(57) ABSTRACT

A combustible gas sensor for detecting an analyte gas includes a first element including a first electric heating element, a first support structure on the first electric heating element and a first catalyst supported on the first support structure and electronic circuitry in electrical connection with the first element. The electronic circuitry is configured to provide energy to the first element to heat the first element to at least a first temperature at which the first catalyst catalyzes combustion of the analyte gas and to determine if the analyte gas is present based on a response of the first element to being heated to at least the first temperature. The electronic circuitry is further configured to apply an interrogation pulse to the first element in which energy to the first element is increased or decreased to induce an associated response from the first element.

26 Claims, 16 Drawing Sheets

(56) References Cited

U.S. PATENT DOCUMENTS

| | | | |
|---|---|---|---|
| 5,528,225 A | 6/1996 | Sakai | |
| 5,599,584 A | 2/1997 | Champney, Jr. | |
| 5,780,715 A | 7/1998 | Imblum | |
| 6,131,438 A | 10/2000 | Zanini-Fisher | |
| 6,705,152 B2 | 3/2004 | Routkevitch | |
| 8,826,721 B2 | 9/2014 | Zanella, Sr. | |
| 2002/0146352 A1 | 10/2002 | Wang | |
| 2008/0034841 A1 | 2/2008 | Bahs | |
| 2009/0324449 A1* | 12/2009 | Kira | G01N 27/16 422/96 |
| 2011/0100090 A1 | 5/2011 | Zanella, Sr. | |
| 2012/0318037 A1 | 12/2012 | Lee | |
| 2014/0273263 A1 | 9/2014 | Zanella, Sr. | |
| 2018/0128763 A1 | 5/2018 | Swanson | |

FOREIGN PATENT DOCUMENTS

| | | |
|---|---|---|
| JP | 2000039413 | 2/2000 |
| WO | WO2018085026 | 5/2018 |
| WO | WO2018212965 | 11/2018 |
| WO | WO2018212966 | 11/2018 |

OTHER PUBLICATIONS

Firth, J.G. et al., Combustion and Flame 21, 303 (1973).
Mosely, P.T. and Tofield, B.C., ed., Solid State Gas Sensors, Adams Hilger Press, Bristol, England (1987).

* cited by examiner

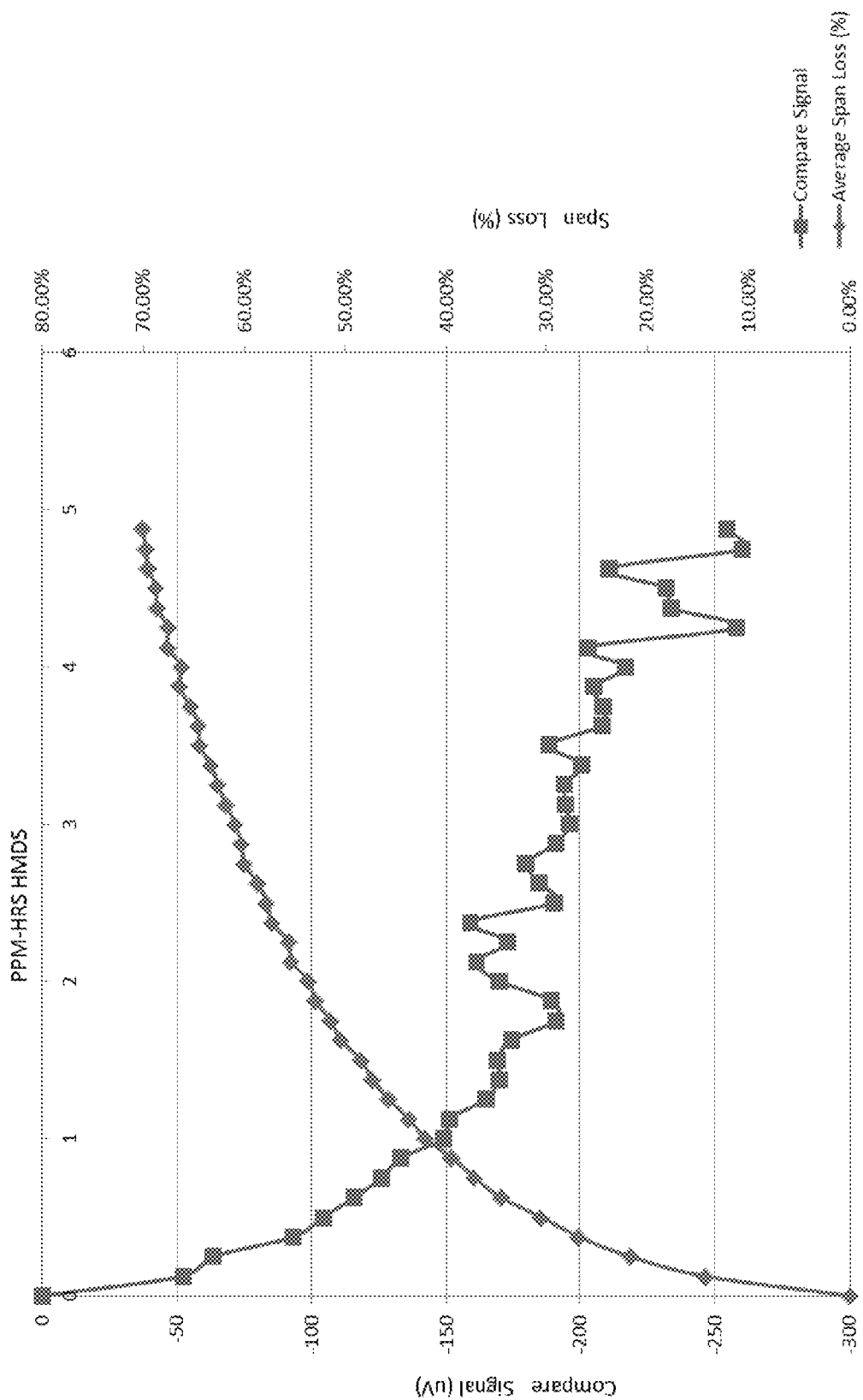

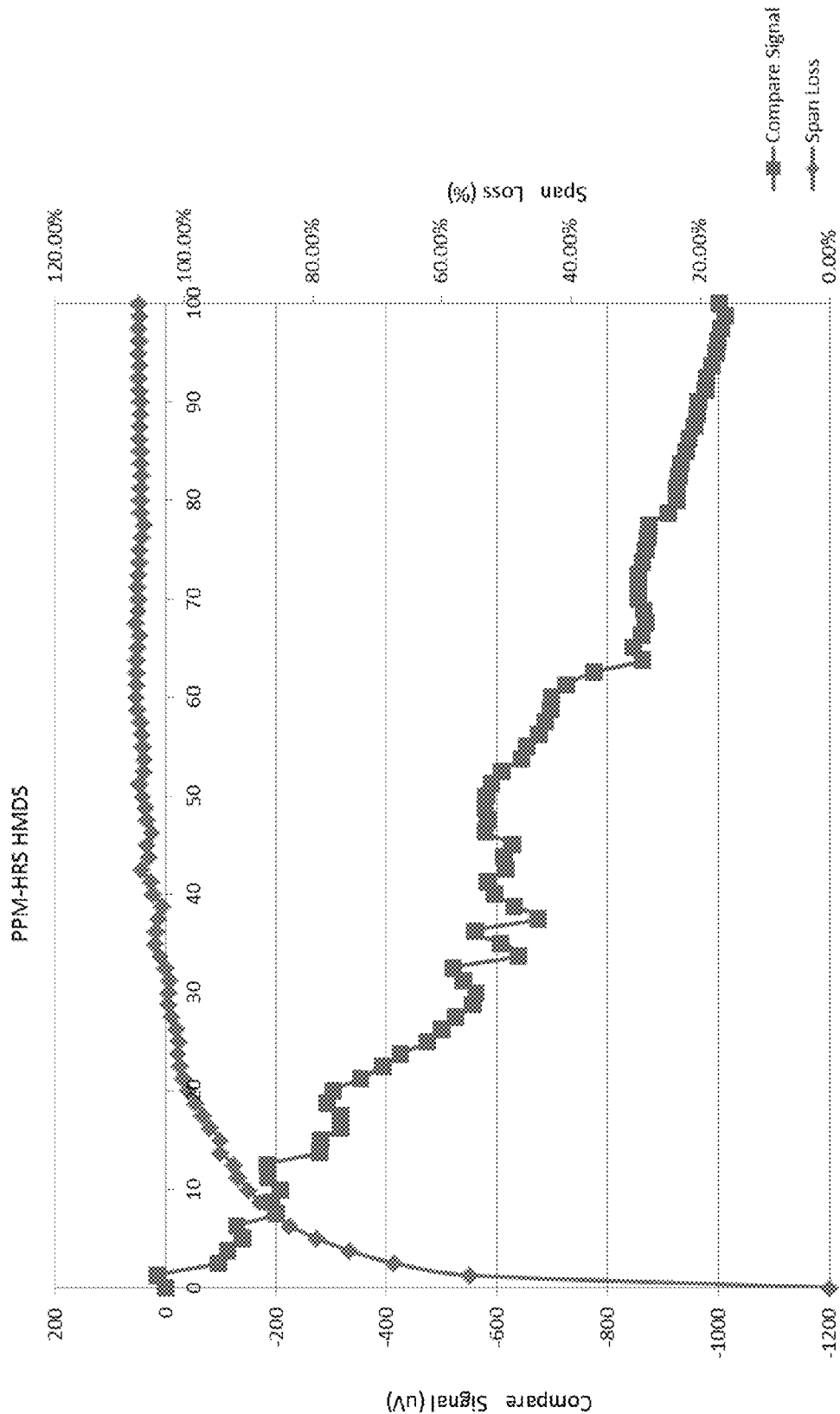

DYNAMIC COMPARATIVE DIAGNOSTICS FOR CATALYTIC STRUCTURES AND COMBUSTIBLE GAS SENSORS INCLUDING CATALYTIC STRUCTURES

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases.

The operation of a catalytic combustible gas sensor proceeds through electrical detection of the heat of reaction of a combustible gas on the oxidation catalyst, usually through a resistance change. The oxidation catalysts typically operate in a temperature above 300° C. to catalyze combustion of an analyte (for example, in the range of 350 to 600° C. temperature range for methane detection). Therefore, the sensor must sufficiently heat the sensing element through resistive heating. In a number of combustible gas sensors, the heating and detecting element are one and the same and composed of a platinum alloy because of its large temperature coefficient of resistance and associated large signal in target/analyte gas. The heating element may be a helical coil of fine wire or a planar meander formed into a hotplate or other similar physical form. The catalyst being heated often is an active metal catalyst dispersed upon a refractory catalyst substrate or support structure. Usually, the active metal is one or more noble metals such as palladium, platinum, rhodium, silver, and the like and the support structure is a refractory metal oxide including, for example, one or more oxides of aluminum, zirconium, titanium, silicon, cerium, tin, lanthanum and the like. The support structure may or may not have high surface area (that is, greater than 75 $m^2/g$). Precursors for the support structure and the catalytic metal may, for example, be adhered to the heating element in one step or separate steps using, for example, thick film or ceramic slurry techniques. A catalytic metal salt precursor may, for example, be heated to decompose it to the desired dispersed active metal, metal alloy, and/or metal oxide.

As illustrated in FIGS. 1A and 1B, a number of conventional combustible gas sensors such as illustrated sensor 10 typically include an element such as a platinum heating element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity, and pressure.

To minimize the impact of secondary effects on sensor output, the rate of oxidation of the combustible gas may, for example, be measured in terms of the variation in resistance of sensing element or pelement 40 relative to a reference resistance embodied in an inactive, compensating element or pelement 50. The two resistances may, for example, be part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. In a number of systems, compensating pelement 50 may, however, either carry no catalyst or carry an inactivated or poisoned catalyst. In general, changes in properties of compensating elements caused by changing ambient conditions are used to adjust or compensate for similar changes in the sensing element.

Catalytic combustible gas sensors are typically used for long periods of time over which deterioration of the sensing element or the like and malfunction of circuits may occur. A foreign material or contaminant such as an inhibiting material or a poisoning material (that is, a material which inhibits or poisons the catalyst of the sensing element) may, for example, be introduced to the sensing element. An inhibiting material typically will "burn off" over time, but a poisoning material permanently destroys catalytic activity of the sensing element. Inhibiting materials and poisoning materials are sometimes referred to herein collectively as "poisons" or "poisoning material." In general, it is difficult to determine such an abnormal operational state or status of a combustible gas sensor without knowingly applying a test gas to the combustible gas sensor. In many cases, a detectable concentration of a combustible gas analyte in the ambient environment is a rare occurrence. Testing of the operational status of a combustible gas sensor typically includes the application of a test gas (for example, a gas including a known concentration of the analyte or a simulant thereof) to which the combustible gas sensor is similarly responsive) to the sensor. Periodic testing using a combustible gas may, however, be difficult, time consuming and expensive.

For decades, combustible gas sensor designers have been perplexed with the problems of contamination and/or degradation of their catalyst structures. Sulfur-containing compounds (inhibitors) have been known to target and inhibit the catalyst structures. Filtering techniques are generally used to prevent their passage into the structure. If they do enter the structure, they are bound until a sufficient level of heat is applied to promote their release or decomposition. Volatile silicon/organosilicon compounds (poisons) are also known to cause significant issues with catalytic structures as they are permanently retained, and eventually result in the total inactivity of the catalyst. Further, high levels of hydrocarbons can also deposit incomplete and/or secondary byproducts such as carbon within the structure. Lead compounds, organophosphates and halogenated hydrocarbons are also known to poison/inhibit catalysts used in combustible gas sensors.

Manufacturers may add a layer of inhibitor/poison absorbing material outside of the supported catalyst of a sensing element as well as a compensating element. However, exposure to a sufficient amount of inhibitor/poison can still render the catalyst inactive. Moreover, increasing the mass of the sensing/compensating element increases the power requirements of the sensor, which may be undesirable, particularly in the case of a portable or other combustible gas sensor in which battery power is used.

Moreover, an inhibited or poisoned sensing element may go undetected by, for example, high sensitivity bridge and other circuits used in combustible gas sensors. Users have long reported cases where their catalytic sensors are reading zero (that is, the bridge circuitry is balanced), yet the sensors show little response to gas challenges. A notable example of this effect occurs when an organosilicon vapor such as hexamethyldisiloxane (HMDS) is introduced to the sensor. The HMDS will indiscriminately diffuse into the sensor housing and surroundings, adsorb onto the surface of the detector and/or compensator, and oxidize into a layer of silica (silicon dioxide or $SiO_2$). Since both elements are typically operated at similar temperatures, silicone deposition occurs at an equal rate, keeping the bridge in balance. Unfortunately, this renders the elements permanently inactive. Indeed, some manufacturers use this poisoning process to manufacture compensating elements or compensators for combustible gas sensors.

A number of methods and systems have been developed to sense inhibition/poisoning in a catalytic sensing element with only limited success. Recent advancements include, for example, methods utilizing additional or alternative electrical properties of the catalytic structure such as reactance to analyze one or more variables related to reactance. While such systems and methodologies are able to diagnose the deposition of poisons and inhibitors within the structure of an element for a combustible gas sensor, such systems and methodologies find limited success in detecting the deposition or formation of surface materials which can also block the sensing elements ability to interact with the target gas. It remains desirable to develop diagnostic systems and methods for catalytic sensors and structures to detect inhibition/poisoning.

SUMMARY

In one aspect, a combustible gas sensor for detecting an analyte gas includes a first element. The first element includes a first electric heating element, a first support structure on the first electric heating element and a first catalyst supported on the first support structure. The combustible gas sensor further includes electronic circuitry in electrical connection with the first element. The electronic circuitry is configured to provide energy to the first element to heat the first element to at least a first temperature at which the first catalyst catalyzes combustion of the analyte gas and to determine if the analyte gas is present based on a response of the first element to being heated to at least the first temperature. The electronic circuitry is further configured to apply an interrogation pulse to the first element in which energy to the first element is increased or decreased to induce an associated response from the first element. The electronic circuitry is also configured to analyze the associated response and to determine from the associated response if poisoning or inhibiting of the first catalyst has occurred. In that regard, one or more thresholds for changes in response or changes in values may, for example, be established which are predetermined to indicate if a change in mass of an element has occurred. For example, thresholds for changes in response such as change in slope of a curve, changes in area under the curve, and/or changes in values at one or more times along the curve may be predetermined.

The energy may, for example, be increased in the interrogation pulse such that temperature of the first element is increased to induce joule heating and for sufficient time to induce convective heat transfer between the first support structure and surrounding gas. Alternatively, the energy may, for example, be decreased in the interrogation pulse such that convective heat transfer between the first support structure and surrounding gas ceases and for sufficient time so that the temperature of the first element decreases below the temperature at which joule heating of the first element occurs.

In a number of embodiments, the combustible gas sensor further includes a second element including a second electric heating element and a second support structure on the second electric heating element. The electronic circuitry is in electrical connection with the second element and is configured to operate the second element to compensate for ambient conditions. The second element may, for example, be maintained below a temperature at which catalyst inhibiting compositions or catalyst poisoning compositions are oxidized on the second support structure (for example, while the first element is heated to the first temperature and during the interrogation pulse). The temperature of the second element may, for example, be maintained below 150° C. or below 90° C.

The temperature of the first element may, for example, be increased (via the interrogation pulse) to induce joule heating and for sufficient time to raise the temperature of the first element to at least the first temperature. If the electronic circuitry determines that the analyte gas is present after the temperature of the first element is raised to at least the first temperature, the associated dynamic response resulting from the increasing the temperature of the first element to induce joule heating is disregarded in analyzing the associated dynamic response to determine if inhibiting or poisoning has occurred.

In a number of embodiments, the energy is decreased in the interrogation pulse from a temperature of at least the first temperature such that convective heat transfer between the first support structure and surrounding gas ceases and for sufficient time so that the temperature of the first element decreases below the temperature at which joule heating of the first element occurs. The energy may, for example, be decreased in the interrogation pulse only after a determination by the electronic circuitry that analyte gas is not present.

In a number of embodiments, the electronic circuitry is configured to apply a plurality of interrogation pulse to the first element over time in which energy to the first element is increased or decreased to induce an associated response from the first element in each of the plurality of interrogation pulses. The electronic circuitry is configured to analyze one or more of the associated responses and to determine from the associated responses if poisoning or inhibiting of the first catalyst has occurred.

In another aspect, a method of operating a combustible gas sensor for detecting an analyte gas is set forth. The combustible gas sensor includes a first element including a first electric heating element, a first support structure on the first electric heating element and a first catalyst supported on the first support structure. The combustible gas sensor further includes electronic circuitry in electrical connection with the first element. The method includes operating the electronic circuitry to provide energy to the first element to heat the first element to at least a first temperature at which the first catalyst catalyzes combustion of the analyte gas and to determine if the analyte gas is present based on a response of the first element to being heated to at least the first temperature, operating the electronic circuitry to apply an interrogation pulse to the first element in which energy to the first element is increased or decreased to induce an associated response from the first element, and analyzing the associated response to determine if poisoning or inhibiting of the first catalyst has occurred.

The energy may, for example, be increased in the interrogation pulse such that temperature of the first element is increased to induce joule heating and for sufficient time to induce convective heat transfer between the first support structure and surrounding gas. Alternatively, the energy may, for example, be decreased in the interrogation pulse such that convective heat transfer between the first support structure and surrounding gas ceases and for sufficient time so that the temperature of the first element decreases below the temperature at which joule heating of the first element occurs.

In a number of embodiments, the combustible gas sensor further includes a second element including a second electric heating element and a second support structure on the second electric heating element. The electronic circuitry is in electrical connection with the second element and is configured to operate the second element to compensate for ambient conditions. A temperature of the second element may, for example, be maintained below a temperature at which one or more predetermined catalyst inhibiting compositions or catalyst poisoning compositions are oxidized on the second support structure. In a number of embodiments, the temperature of the second element is maintained below 150° C. or below 90° C.

The temperature of the first element may, for example, be increased via the interrogation pulse to induce joule heating and for sufficient time to raise the temperature of the first element to at least the first temperature. If the electronic circuitry determines that the analyte gas is present after the temperature of the first element is raised to at least the first temperature, the associated response resulting from the increasing the temperature of the first element to induce joule heating and to raise the temperature of the first element to at least the first temperature is disregarded (that is, the associated dynamic response is not analyzed to determine if poisoning or inhibition has occurred).

Energy may, for example, be decreased in the interrogation pulse from a temperature of at least the first temperature such that convective heat transfer between the first support structure and surrounding gas ceases and for sufficient time so that the temperature of the first element decreases below the temperature at which joule heating of the first element occurs. The energy may, for example, be decreased in the interrogation pulse only after a determination by the electronic circuitry that analyte gas is not present.

In a number of embodiments, the method further includes applying a plurality of interrogation pulses to the first element over time in which energy to the first element is increased or decreased to induce an associated response from the first element in each of the plurality of interrogation pulses and analyzing one or more of the associated responses and to determine from the associated responses if poisoning or inhibiting of the first catalyst has occurred.

In a further aspect, a combustible gas sensor for detecting an analyte gas includes a first element. The first element includes a first electric heating element, a first support structure on the first electric heating element and a first catalyst supported on the first support structure. The combustible gas sensor also includes a second element including a second electric heating element and a second support structure on the second electric heating element. The combustible gas sensor further includes electronic circuitry in electrical connection with the first element and the second element. The electronic circuitry is configured in a first mode to provide energy to the first element to heat the first element to at least a first temperature at which the first catalyst catalyzes combustion of the analyte gas and to determine if the analyte gas is present based on a response of the first element to being heated to at least the first temperature. The electronic circuitry is further configured in a second mode to apply an interrogation pulse to the first element in which energy to the first element is increased or decreased to induce an associated response from the first element. The electronic circuitry is also configured to analyze the associated response and to determine from the associated response if poisoning or inhibiting of the first catalyst has occurred. The second element is operated below a temperature at which one or more predetermined catalyst inhibiting compositions or catalyst poisoning compositions are oxidized on the second support structure in the first mode and in the second mode. The second element may, for example, be maintained below 150° C. for below 90° C.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 7 illustrates the response to application of 15 ppm HMDS of the electronic circuitry of FIG. 6A in a first or gas detection mode and in a second or compare mode.

FIG. 8 illustrates the response to long term application of 15 ppm HMDS of the electronic circuitry of FIG. 6A in the first or gas detection mode and in the second or compare mode.

DETAILED DESCRIPTION

Figure 1B:
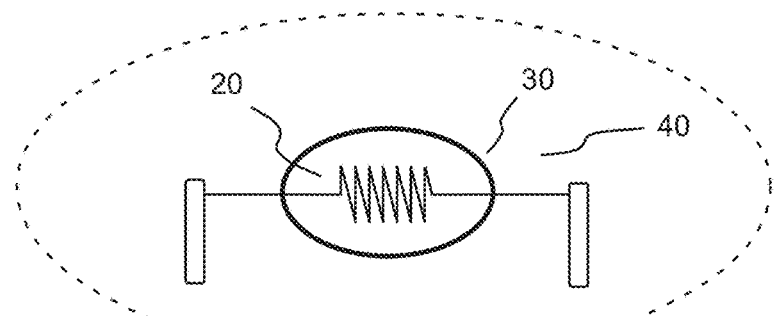
FIG. 1B illustrates an enlarged view of the active sensing element, pelement or detector of the combustible gas sensor of FIG. 1A.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etcetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensing element" includes a plurality of such sensing element and equivalents thereof known to those skilled in the art, and so forth, and reference to "the sensing element" is a reference to one or more such sensing elements and equivalents thereof known to those skilled in the art, and so forth.

The terms "electronic circuitry", "circuitry" or "circuit," as used herein includes, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiments hereof, devices, systems and method of determining the well-being or operational status of a catalytic structure (for example, a sensing element in a combustible gas sensor) are set forth that do not require the use or application of the analyte (or target) gas, a simulant thereof (that is, the application of a test gas is not required) or any other gas to a sensor. The catalytic structures or elements hereof generally include a heating element (typically a conductive element), an insulating support structure disposed on the heating element, and a catalyst disposed upon the support structure.

In a number of representative studies set forth herein, comparative methods or measurements are determined. One skilled in the art appreciates that a number of different variables related to or relatable to a change in thermal properties of an element (for example, a combustible gas sensing element) associated with a change in mass of the element may be used. Changes in such variables are, for example, related to or indicative of a change in mass resulting from the presence of a contaminant on the catalytic structure of a sensing element and/or to the sensitivity of a sensing element for an analyte. In a number of embodiments, changes in an electrical property such as resistance of an element is monitored. A variable such as voltage, current or resistance may, for example, be measured depending upon the manner in which the electrical circuitry of the sensor is controlled. For example, voltage or current in an electronic circuit can be measured and related to a change in resistance of an element. Alternatively, electronic circuitry of a sensor may be driven to maintain resistance of the element relatively constant and a voltage or a current may be measured.

Figure 2:
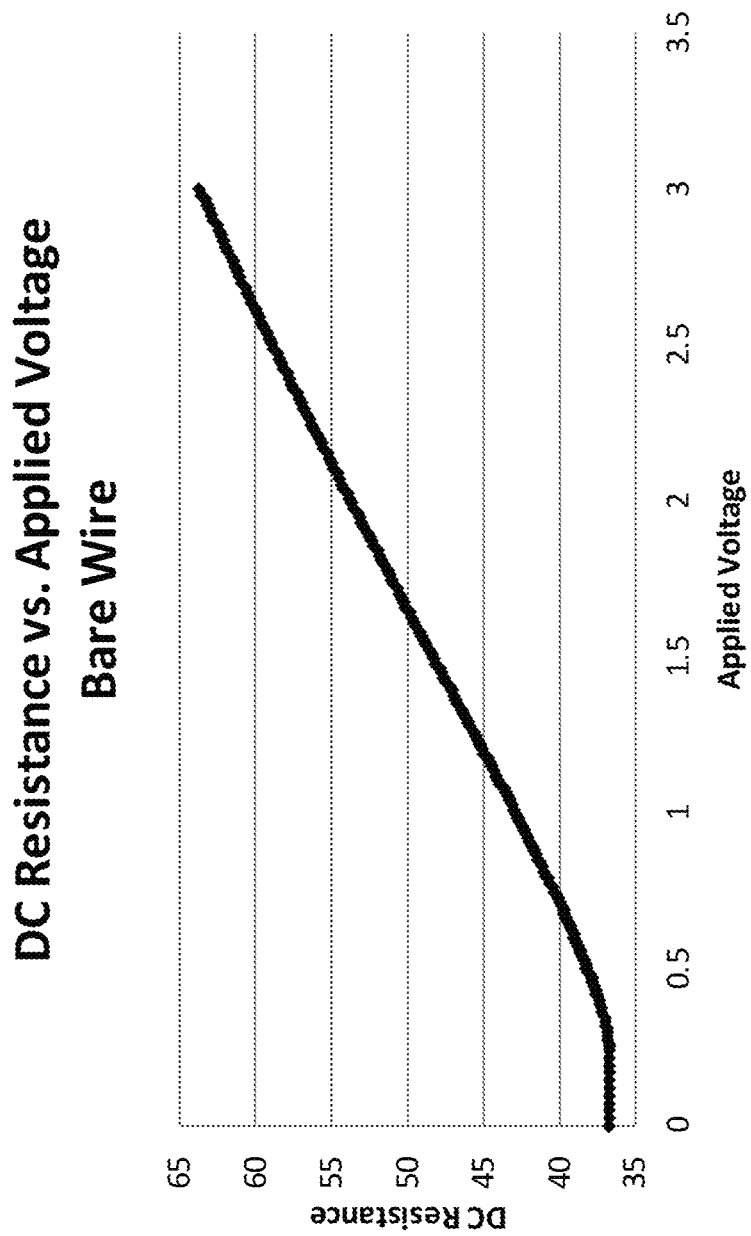
FIG. 2 illustrates an embodiment or element such as a platinum alloy heating element wire or coil and the response associated with applying a DC voltage.

FIG. 2 illustrates the response of an element such as a platinum heating element wire or coil 20 associated with applying an increasing DC voltage at a fixed temperature. During the application of low voltages (0V-0.25V in the illustrated example), the element resistance remains consistent. In this voltage range, resistive changes are predominantly governed by ambient temperature fluctuations. The principles employed in this regime are well known and are used, for example, in resistive thermometers. In that regard, the platinum resistance thermometer is a versatile instrument for temperature measurement in the range from approximately −200° C. to +1000° C. One may, for example, use the simplified Callendar-Van Dusen equation to determine the temperature dependent resistance as follows:

$$R_t = R_0[1+\alpha(t-t_0)]$$

wherein $R_t$ is the resistance of the element at temperature t, $R_0$ is the resistance at a standard temperature $t_0$, and $\alpha$ is the temperature coefficient of resistance. The above principle may, for example, be used as described in U.S. Pat. No. 8,826,721, the disclosure of which is incorporated herein by reference, to operate a sensor element in a low power (voltage) mode in which the sensor element including an active catalyst is able to function as a compensating element or compensator.

Referring again to FIG. 2, the application of higher voltages (>0.5V in the representative example of FIG. 2) will cause the wire to increase in temperature, and thus in resistance. This effect is known as Joule's first law or the Joule-Lenz law. Joule heating, also known as ohmic heating or resistive heating, is the process by which the passage of an electric current through a conductor releases heat. In the case of a sensor element including a catalyst support structure, the heat transfer from the heating element/wire will eventually reach an equilibrium as the heat will conduct from the heating element to the support structure of the sensing element (including, for example, a refractory support structure and a catalyst supported thereof) and then via fluidic convection through the surrounding gases. Thermal equilibrium will remain balanced until (a) the ambient temperature changes; (b) the makeup of the surrounding gas mixture is altered, or (c) the transfer of heat between the wire and the mass of the element changes (as a result of a mass or density change). These effects are all competing and interacting effects.

In the case of a combustible gas sensor, a heating element such as heating element 20 of FIG. 1B (for example, a conductive wire, coil or surface) is used to sufficiently raise the structure of the element (including the support structure and catalyst) to a temperature to promote the catalytic reaction of the analyte or target gas. As used herein with respect to an element hereof (that is, a sensing element or a compensating element), temperature refers to an average temperature over the volume of the element. Heating elements have generally been made from coils, and over time smaller diameter wires have been used to reduce the power consumption of the element.

Figure 1A:
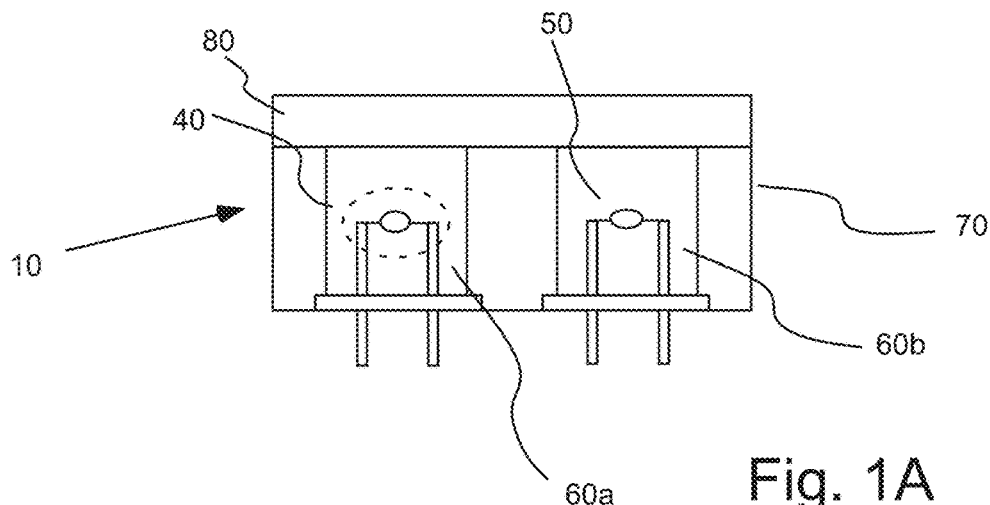
FIG. 1A illustrates an embodiment of a currently available combustible gas sensor.
Figure 3A:
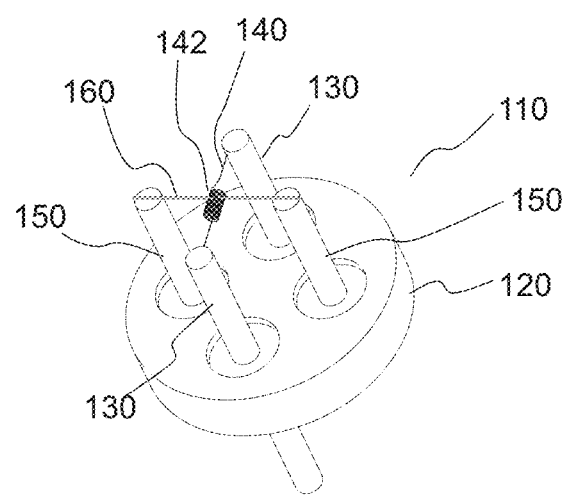
FIG. 3A illustrates a perspective view of an embodiment of a detector assembly wherein a sensing element is supported by a supporting wire.
Figure 3B:
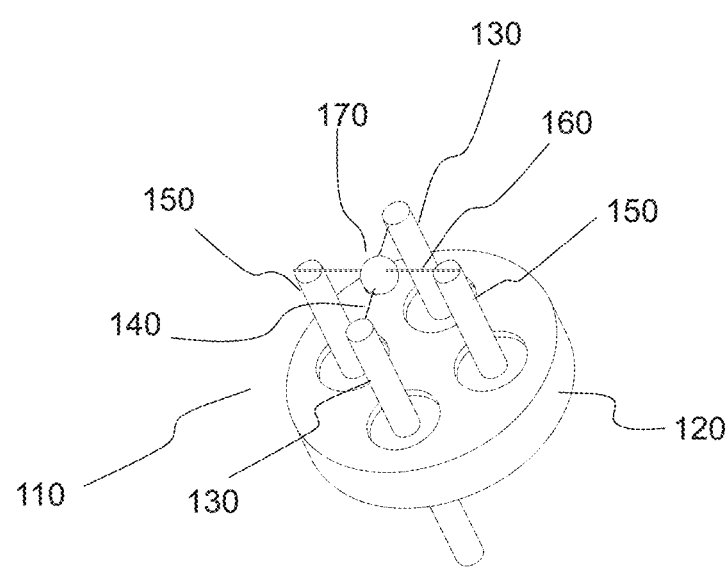
FIG. 3B illustrates a perspective view of the detector assembly of FIG. 3A including a ceramic bead (upon which a catalyst is supported) formed over the sensing element wire.
Figure 3C:
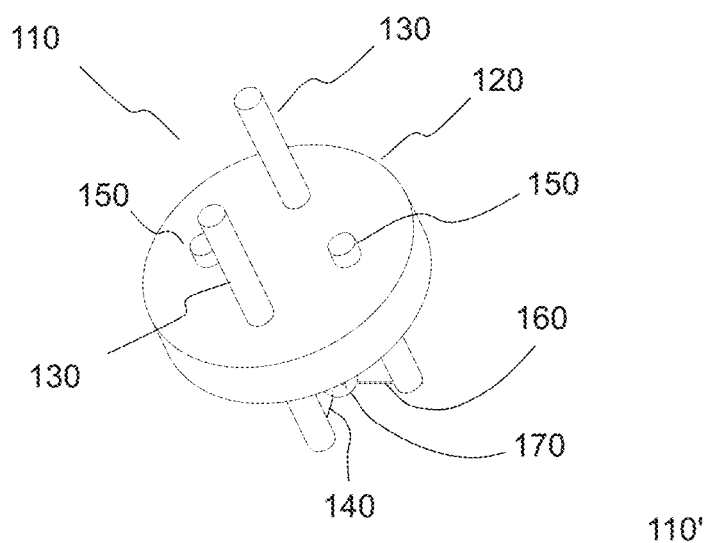
FIG. 3C illustrates another perspective view (generally opposite that of FIG. 3B) of the detector assembly of FIG. 3A.

The use of conductive elements such as wires having relatively small diameter in element for combustible gas sensors is, for example, disclosed in U.S. Pat. No. 8,826,721. In that regard, FIGS. 3A through 3C illustrate a representative embodiment of a detector/element assembly 110 which may, for example, be used in a gas sensor as illustrated in FIG. 1A. Element assembly 110 includes a base 120 to which two electrically conductive contact members 130 (extending members or posts in the illustrated embodiment) are attached. A sensing conductive element 140 is connected between contact members 130, wherein each end of conductive elements 140 is connected to or anchored to one of contact members 130. In the illustrated embodiment, conductive element 140 includes an intermediate section including a coiled section 142 that can, for example, be located approximately centrally between the ends of conductive element 140. Wires and/or other conductive elements for heating elements are selected to have a favorable temperature coefficient for sensing applications and are generally a precious metal or alloy.

Element assembly 110 further includes two support members 150 (extending members or posts in the illustrated embodiment) connected to base 120. In the illustrated embodiment, a support member or element 160 in the form of, for example, a wire, a ribbon, a rod or other suitable support structure or material extends between support members or posts 150. Base 120, contact members 130 and support members 150 can, for example, be formed of a metal such as KOVAR® (a nickel-cobalt ferrous alloy designed to be compatible with the thermal expansion characteristics of borosilicate glass) available from Carpenter Technology Corporation of Reading, Pa. Contact members 130 and support members 150 can, for example, be sealed to base 120 using a glass such as borosilicate glass to provide electrical isolation.

Using a strong yet relatively thin support element 160 anchored, connected or attached at each end thereof (for example, anchored at two support members or posts 150) prevents bead movement in all three dimensions while limiting heat loss. In the illustrated embodiment of FIGS. 3A through 3C, support element 160 passes through and contacts one of the coils of coiled section 142. Contact between support element 150 and conductive element 140 is thus minimal. As described below, support element 150 need not contact conductive element 140 to provide support therefor, but can contact or pass through a catalyst support member or structure 170 encompassing conductive element 140.

A balance may, for example, be established between the tensile strength and the thermal conductivity to achieve an effective result for support element 150. In general, a quotient or ratio calculated by dividing the tensile strength in units of pounds per square inch of psi by the thermal conductivity in units of watts/cm/° C. may, for example, be at least 250,000, at least 400,000 or even at least 500,000. For example, in several studies, a support element in the form of a wire made from an alloy of platinum and tungsten had a tensile strength of 250,000 psi and a thermal conductivity of 0.5 watts/cm/° C., resulting in a quotient of 500,000. For support elements having a higher tensile strength, a higher thermal conductivity may be acceptable since support elements of smaller average diameter (or average cross-sectional area) can be used (resulting in less mass to conduct heat away from the sensing element). Moreover, reducing the size/volume of the element reduces the effect of ambient humidity and pressure changes on the sensor. For example, in the case of a tungsten support element having a tensile strength of 600,000 psi and a thermal conductivity of 1.27 watts/cm/° C., a smaller average diameter support element can be used to achieve a similar result to that achieved with the platinum-tungsten alloy support element described above. Alternatively, one could also choose a support element of an alloy of platinum with 20% iridium having a larger average diameter. Such a platinum-iridium alloy has a tensile strength of 120,000 psi and a thermal conductivity of 0.18 watts/cm/° C. Metal support elements or metal alloy elements having the above-described properties can be used to maximize strength/support while minimizing heat loss.

In that regard, in several embodiments, support element 160 exhibits relatively high strength (for example, having a tensile strength of at least 100,000 psi, at least 250,000 psi, or even at least 400,000 psi) as well as low thermal conductivity (for example, having a thermal conductivity less than 1.5 less watts/cm/° C., less than 0.5 watts/cm/° C., no greater than 0.25 watts/cm/° C., or even no greater than 0.10 watts/cm/° C.) to provide a quotient as described above. In a number of embodiments, the average diameter of support element 160 (in the case of a support element of a generally circular cross-section) is in the range of approximately 0.0005 (12.7 μm) to 0.0025 inches (63.5 μm). In the case of support elements having a noncircular cross-section, the average cross-sectional area can, for example, be in the range of the average cross-sectional area of an element of generally circular cross-section having an average diameter in the range of approximately 0.0005 to 0.0025 inches. References herein to elements having a certain average diameter are also references to elements having a generally noncircular cross-section, but having an average cross-sectional area equivalent to the average cross-sectional area provided by the stated average diameter. In several representative studies, an in-molded wire was used as support element 160. In several such embodiments, a platinum-tungsten alloy support element 160 having an average diameter of approximately (that is, within 10% of) 0.001 inches (63.5 μm) provided a robust support, and did not result in measurable additional power required to operate sensing element 140. Alloys of tungsten, nickel, molybdenum or titanium with, for example, platinum, palladium or rhodium can, for example, be used in support element 160.

As illustrated in FIG. 3B, catalyst support structure 170 (for example, a ceramic bead in a number of embodiments) can be formed on coil section 120 of sensing conductive element 140 to support a catalyst and form a sensing element/pelement. In forming catalyst support structure 170 as a refractory material such as a ceramic bead, an aluminum oxide suspension may, for example, be fired onto coiled section 142. The resultant catalyst support structure/ceramic bead 170 may be impregnated with a catalyst. Although a bare wire comprising a catalytic material (such as platinum) can be used as a sensing element in certain embodiments of a combustible gas sensor, a catalyst support structure 170 (such as a ceramic bead) provides increased surface area for one or more catalyst species.

In the embodiment illustrated in FIGS. 3A through 3C, catalyst support structure 170 is formed over (to encompass) conductive element 140 and support element 160. In a number of embodiment, support element 160 need not contact conductive element 140 to provide support therefor. For example, support element 160 can pass through or contact catalyst support structure 170 without contacting conductive element 140 and indirectly provide support for conductive element 140. To provide support for conductive element 140 in three dimensions, support element 160 preferably passes through catalyst support structure 170.

The support assembly, including, for example, support member 150 and support element 160, enables the use of a sensing element 140 having a relatively small average diameter. For example, a wiring having an average diameter no greater than approximately 20 μm of 10 μm may be used. Such a small average diameter wire (with a corresponding higher per unit length resistance than larger diameter wires) lends itself well to reducing the required operating current (which is very desirable in portable applications), and thus the required power levels.

In a number of embodiments, the support members or catalyst support members hereof have a volume less than a sphere having a diameter of 500 μm (wherein the volume of a sphere is calculated by the formula $4/3 \times \pi \times (D/2)^3$, that is, less than $6.5 \times 10^7$ μm$^3$). The first catalyst support member can have a volume no greater than a sphere having a diameter of no greater than 440 μm (that is, less than $4.46 \times 10^7$ μm$^3$), or a diameter no greater than 300 μm (that is, less than $1.4 \times 10^7$ μm$^3$).

Figure 3D:
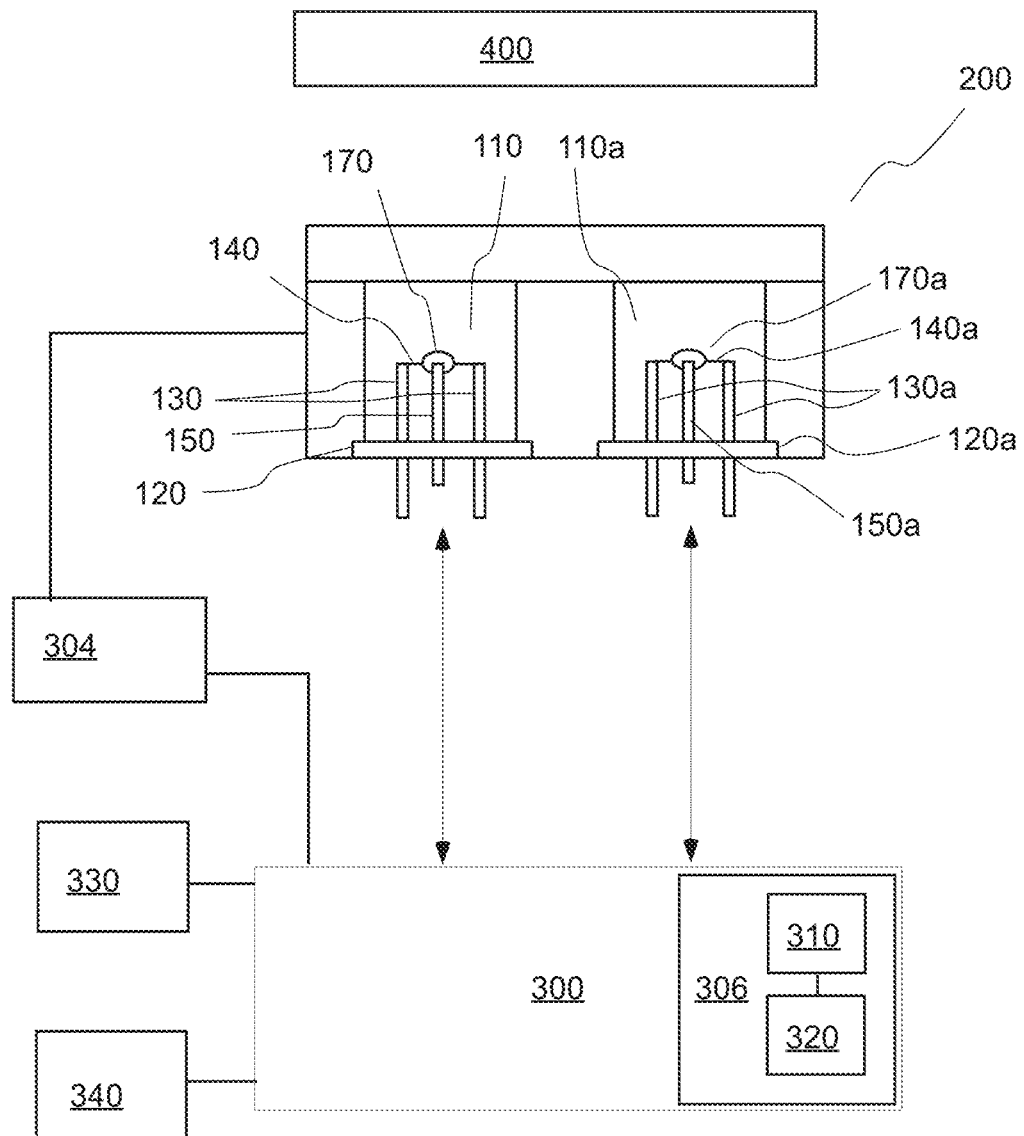
FIG. 3D illustrates a combustible gas sensor including two detector assemblies of FIG. 3B in electrical connection with control and measurement circuitry (illustrated schematically).

A sensor or sensor assembly 200 as illustrated in FIG. 3D may be made which includes two element/detector assemblies 110 (first element) and 110a (second element; in FIG. 3D, elements of second element 110a are numbered similarly to like elements of first element 110, with addition of the designation "a" thereto). Electronic circuitry 300 may be placed in electrical connection with contact posts 130 and 130a of each of element assemblies 110. In the case of a sensor fixed at a position within a facility, power may be provided from a remote source. As described above, in the case of a portable sensor, power source 304 may include one or more batteries. As also described above, the sensor system may also include a control system 306 which may, for example, include control circuitry and/or one or more processors 310 (for example, a microprocessor) and an associated memory system 320 in communicative connection with processor(s) 310.

Figure 4:
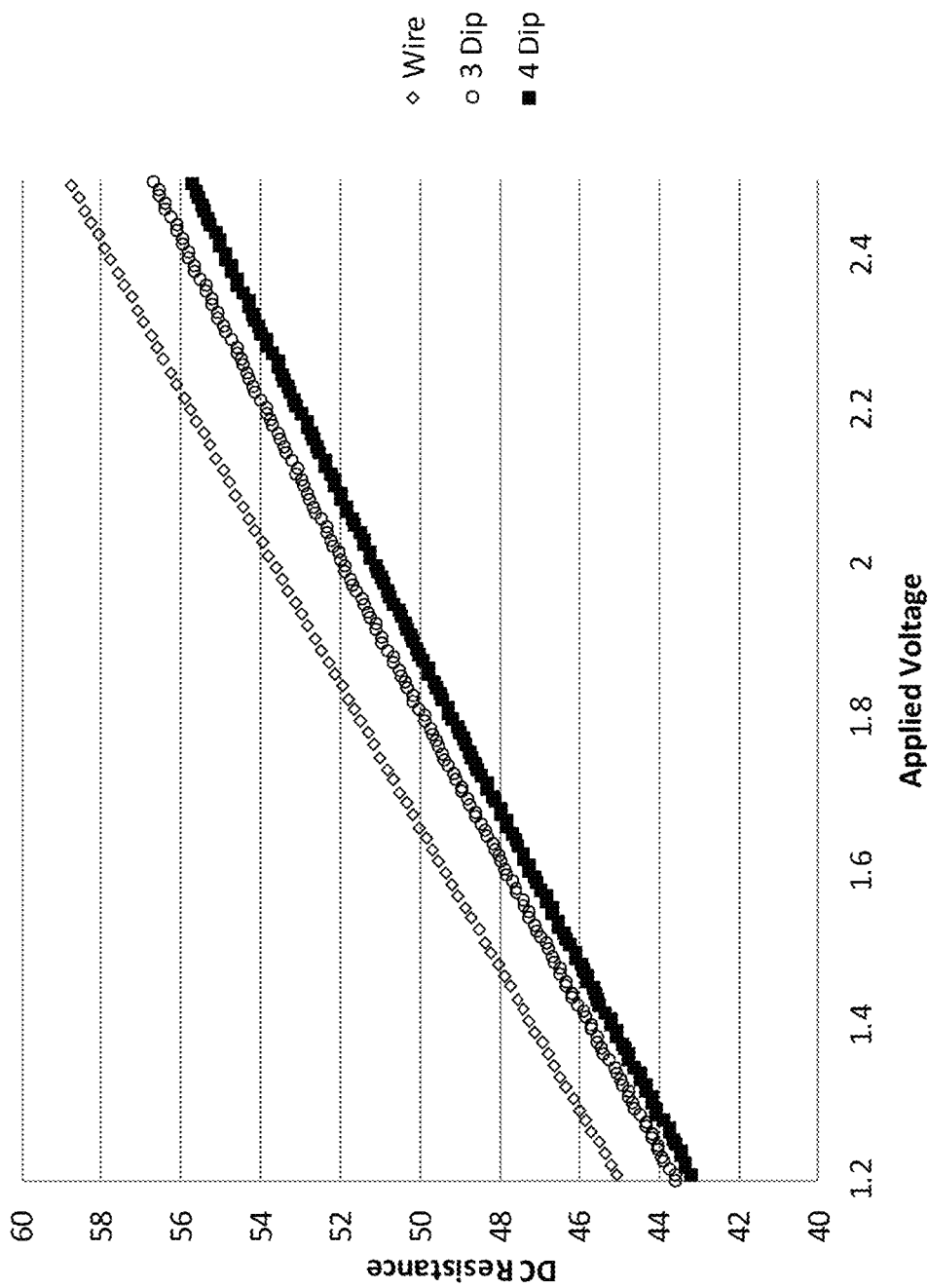
FIG. 4 illustrates the effects of mass loading of refractory materials onto a platinum alloy heating element wire or coil and the response associated with applying a DC voltage.

FIG. 4 illustrates the effects of mass loading on the resistance of a heating element/wire. In that regard, FIG. 4 shows the difference between a bare coiled wire, a coil wire after formation thereon of a refractory support via the application of three dips of a solution of a precursor for a refractory material, and a coil wire after thereon of a refractory support via the application of four dips of refractory materials. As known in the art, a heating element in the form of a wire or wire coil be dipped it into an aqueous solution of a precursor of a refractory. The precursor may then be converted into the refractory material by heating (for example, by the passage of an electrical heating current through the heating element). The dipping process is usually repeated to build up a support structure of the desired size/average diameter around the heating element. A solution or dispersion of a catalyst may then be applied to the outer surface of the support structure. As the mass of the support structure is increased (via increasing the number of dip within precursor material), the heating element (wire or coil) resistance decreases as a function of mass for any given applied voltage (that is, any line drawn parallel to the Y axis in FIG. 4). Mass loading as a result of deposition of an inhibitor or a poison on the support structure also results in a decrease in resistance.

As described above, the operation of a catalytic combustible gas sensor may proceed through electrical detection of the heat of reaction of a combustible gas on the oxidation catalyst (for example, through a resistance change via a Wheatstone bridge). The oxidation catalysts may, for example, operate in the temperature range of 350-600° C. for methane detection. Among common hydrocarbons, methane requires the highest temperature for combustion, hydrogen requires low temperatures, and larger alkanes fall in between, with longer to shorter carbon chain requiring lower to higher light-off temperatures.

The active or sensing element in a number of combustible gas sensors hereof may, for example, be operated at a generally constant voltage, a constant current or a constant resistance (and thereby at a constant temperature) during a particular mode of operation. In a number of embodiments of combustible gas sensors hereof, the electronic circuitry of the combustible gas sensor operates in a first mode in which a first or sensing element is heated to or operated at a temperature at which the first catalyst catalyzes combustion of the analyte gas (for example, above 300° C. for methane). In a second mode, the electronic circuitry operates to heat the sensing element to a second temperature which is lower than the first temperature. The second temperature is below the temperature at which the first catalyst catalyzes combustion of the analyte gas but is at or above a temperature at which Joule heating of the first element occurs. The second temperature may also be below the light off temperature of other combustible gasses that may be in the environment being tested by the sensor. The second temperature is also typically lower than a temperature at which one or more predetermined inhibitors and/or poisons which may be predetermined (for example, inhibitor(s) or poison(s) that may be present in the ambient environment) are deposited/oxidized upon or within the support structure of the first element. Once again, however, the second temperature is at or above the temperature at which Joule heating occurs (see the sloped portion of FIG. 2, for example) so that changes in mass affect the resistance thereof (see FIG. 4, for example).

The electronic circuitry measures a variable in the second mode related to a mass of the first element. The variable is measured over time (that is, through multiple cycles between the first mode and the second mode), and change in the variable over time is analyzed to relate the change in the variable to a change in mass of the first element. The change in mass is an indication of deposition of a poison or inhibitor of the catalyst of the first element. For example, voltage, current or resistance of the second element can be measured (depending upon the manner in which the system is driven to control voltage, current and/or resistance in the second mode).

As described above, the first element will react to changes in various ambient conditions that can change its output in the first mode and/or the second mode (that is, anything that changes the energy balance on the first element). Changes in ambient conditions over time may thereby create errors measurements by the electronic circuitry in the first and/or the second mode or operation. Changes in ambient conditions that effect measurements include changes in ambient temperature, humidity, and/or pressure.

Reducing the size/mass of the sensing element may reduce the effects of such ambient phenomena. In a number of embodiments, however, compensation may be made for changes in ambient conditions in measurements made by the electronic circuitry. One or more such ambient conditions may be measured and one or more algorithms executed to correct measurements by the electronic circuitry. A second or compensating element may also be used to effectively compensate for changes in ambient conditions.

In a number of embodiments, during the first mode of operation as described above, a second or compensating element is operated at a third temperature which is lower than the temperature at which the first catalyst catalyzes combustion of the analyte gas (that, is at a temperature at which the catalyst is substantially or completely inactive to catalyze combustion of the analyte gas). The third temperature may also be below the light off temperature of other combustible gasses that may be in the environment being tested by the sensor. The third temperature may also be lower than a temperature at which one or more inhibitors and/or poisons may be deposited/oxidized upon or within the support structure of the second element (that is, below a temperate at which mass would be added to the second element in the presence of such inhibitors and/or poisons). The third temperature may, for example, be ambient temperature or another temperature associated with a power input below which resistance change/Joule heating occurs in the second element. The second element may, for example, include no catalyst on the support structure thereof, an inactive/poisoned catalyst on the support structure thereof or an active catalyst on the support structure thereof. In a number of embodiments, the second element is closely matched in structure to the first element as known in the art. In the first mode, the first element operates as a sensing element and the second element operates as a compensating element.

In the second mode as described above, the second element is operated at a fourth temperature which is lower than the temperature at which the first catalyst catalyzes combustion of the analyte gas. The fourth temperature is also lower than a temperature at which inhibitors and/or poisons are deposited/oxidized upon or within the support structure of the first element. The fourth temperature may, for example, be ambient temperature or another temperature associated with a power input below which resistance change/Joule heating occurs in the second element. In a number of embodiments, the fourth temperature is a temperature at which Joule heating of the second element occurs. In a number of embodiments, the second temperature and the fourth temperature are equal or substantially equal (that is, differing by no more than 5%, no more than 2% or nor more than 1%). By having the second temperature and the fourth temperature be equal or substantially equal, effects of ambient temperature changes, relatively humidity changes, etc. may be reduced or minimized in measurements hereof, and compensation is simplified. The electronic circuitry is adapted to or operable to measure a variable in the second mode related to a mass of the first element.

In a number of embodiments, while an element hereof is operated as a compensating or compensator element, the operating temperature of that element does not exceed a temperature at which a poison or an inhibitor is deposited/oxidized upon the element. When a compensating element is heated above the temperature at which a poison or an inhibitor is deposited/oxidized upon the element in a sensor system, and particularly if the compensating element is heated to approximately the operating temperature of the sensing element to catalyst combustion of an analyte, both element may be poisoned or inhibited. If both elements are poisoned or inhibited, the elements yield little measurable difference in output.

Figure 5:
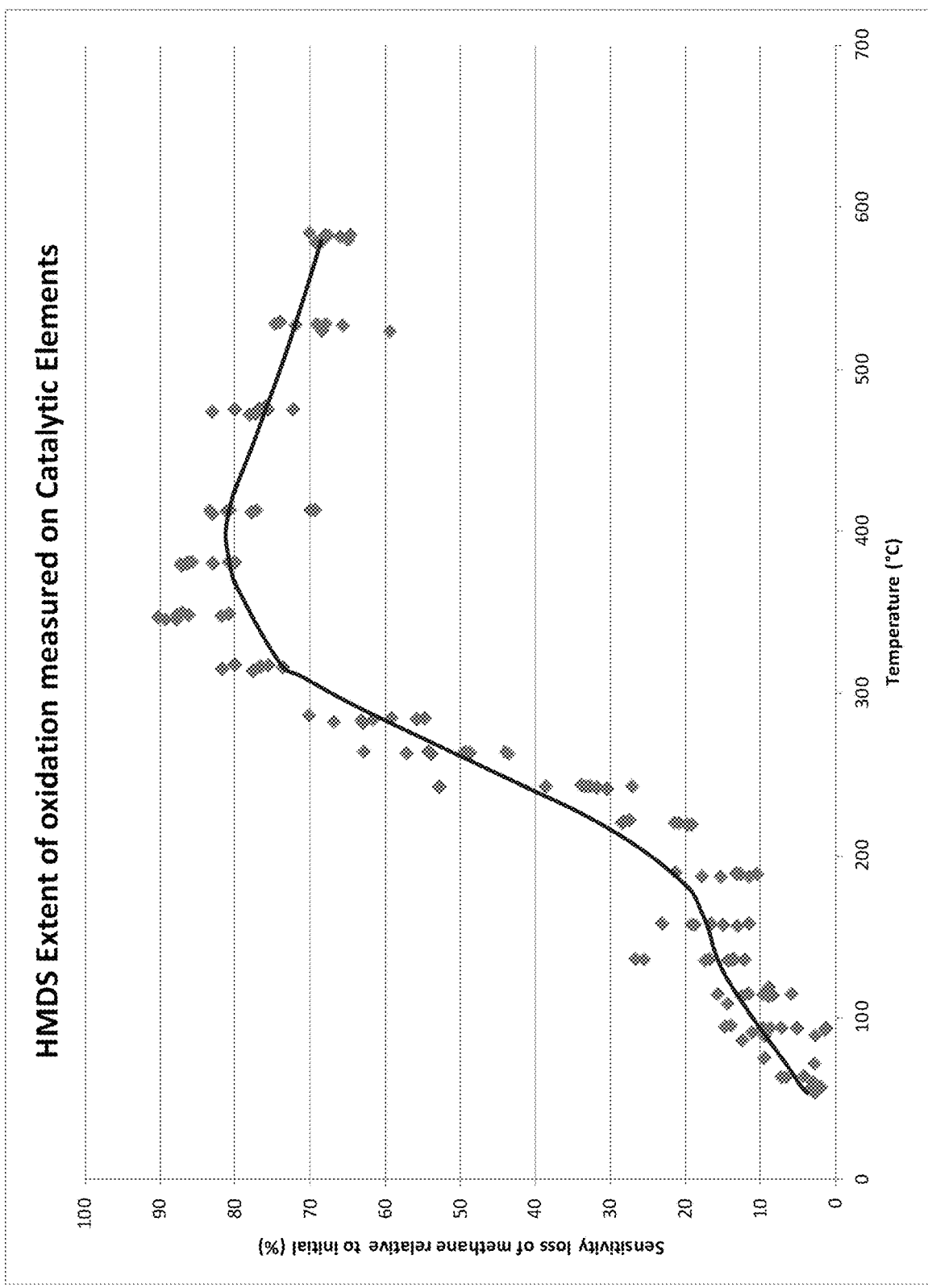
FIG. 5 illustrates a light-off curve for hexamethyldisiloxane (HMDS).

In general, poisons and/or inhibitors are oxidized on the surface of an element (for example, on a support structure of the element) at a certain minimum temperature, sometimes referred to as "light-off" temperature. HMDS is a common poison and has a relatively low light-off temperatures. A light-off curve for HMDS is illustrated in FIG. 5, demonstrating a light-off temperature of greater than 150° C. In a number of embodiments, the third and fourth temperatures of the second element or other element hereof, when operated as a compensator element is less than 150° C. or less than 90° C. In a number of embodiments, the third temperature is approximately ambient temperature. In a number of embodiments, the second temperature of the first element or other element hereof, when operated in the second mode to test for mass change is less than 150° C. or less than 90° C.

Figure 6A:
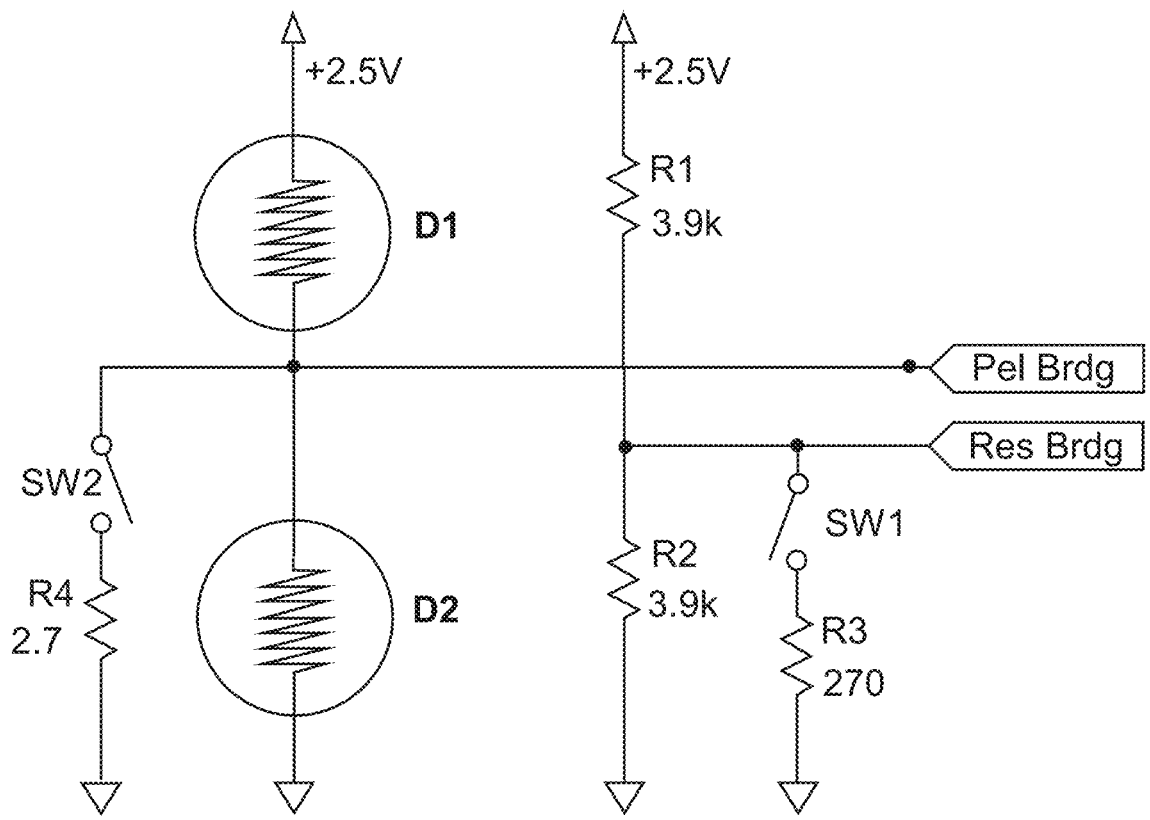
FIG. 6A illustrates a representative circuit diagram of an embodiment of electronic circuitry for use herein in which elements are connected within a bridge circuit.

FIG. 6A illustrates an embodiment of electronic circuitry to enable operation in the first mode and second mode as described above for the evaluation of mass loading on a sensing element, while generally excluding the effects of ambient temperature and the makeup of the surrounding gas mixture. Once again, the mass loading may take the form of poisons or inhibitors attaching to/depositing upon the sensing structure, either internally or on the surface.

In the circuit configuration of FIG. 6A, first element or detector D1 acts as a classical sensing element, and a second element or detector D2 acts as a compensator element. When switches SW1 and SW2 are closed, the bridge circuit operates much like a standard pellistor configuration. In this configuration, there is approximately 100 mV across the compensating element D2 and 2.4V across the sensing element D1. This mode is referred to as the first mode, as described above, or the "gas detection mode." When switches SW1 and SW2 are open, the bridge circuit is operated in the second mode, as described above, or the "comparison mode." In the second or comparison mode, there is approximately 1.25V across each element D1 and D2, which is compared against the two 3.9 kΩ resistors. These two outputs may, for example, be run to a differential amplifier to examine the differences in voltage across the bridge circuit.

In the circuit configuration of FIG. 6A, with switches SW1 and SW2 closed, second element D2 acts as an unheated compensating element. Operating at ambient temperatures (or other temperature below which inhibitors/poisons attached/deposit) prevents second element D2 from being catalytically active (even if an active catalyst is supported thereon) and from poisoned or inhibited as described above. First element D1 functions as a high-temperature sensing element, which exposes first element D1 to poisoning or inhibiting of the catalyst thereof. When switches SW1 and SW2 are opened and the circuit is in second or compare mode, the first and second elements D1 and D2 will reach a thermal equilibrium related to their respective masses. While in compare mode, each of first element D1 and second element D2, may be operated at equal or substantially equal temperature (that is, at a temperature in the Joule heating range) in the embodiment of FIG. 6A, and will thus respond in an equal or substantially equal manner to ambient conditions. If the mass of the active/sensing first element D1 has increased, it will have a lower resistance as compared to previous interrogations, thus creating a change in the bridge balance.

The comparison evaluation may be performed at any applied voltage. The circuit diagram of FIG. 6A uses 1.25V fir the simplicity of explaining the concept.

In the case that second element D2 includes a supported active catalyst, the functions of second element D2 and first element D1 may be switched or cycled so that first element D1 becomes the (high-power/high temperature) sensing element and second element D2 becomes the (low power/low temperature) compensating element. Electronic circuitry 300 (see FIG. 3D), may, for example, effect automatic, periodic switching between sensing element modes as well as periodically switch the function of first element D1 and second element D2. Alternatively or additionally, switching between modes and/or between sensing element functionality can be effected after a manually initiated or controlled event such as a power off/power on (or power cycling) procedure or event. Prior to completion of a switch of the function of first element D1 and second element D2, a comparison mode test should be carried out to ensure that there has been no poisoning of the element that has most recently been operated in the high-power, high-temperature sensing mode. A plurality of sensing elements (for example, three or more) may be used to improve the reliability and ensure the sensors remains on-line for its intended safety purpose. In a number of embodiments hereof, one or more sacrificial or scavenger elements 400 (illustrated schematically in FIG. 3D) can be provided (for example, a heated support structure) having only the function of collecting inhibitors and poisons. Likewise, filters can be provided to filter contaminants such as sulfur, either spaced from an element or on an element.

In a number of embodiments, the second mode as described above is initiated in the interim period between switching the functions of elements such as first element D1 and second element D2. In the case that D1 has most recently been operated in the high power/high temperature mode (that is, at the first temperature as described herein) for catalytic oxidation of the analyte, the temperature of D1 may be decreased to the second temperature as described herein (that is, to a temperature below the temperature at which the analyte is catalytically combusted, but above a temperature at which joule heating occurs). The temperature of D2 is adjusted from the third temperature as described herein to the fourth temperature as described herein (that is, to a temperature below the temperature at which the analyte is catalytically combusted, but above a temperature at which joule heating occurs). Once again, the electronic circuitry hereof measures a variable in the second mode related to a mass of first element D1. The variable is measured over multiple occurrences of the second mode and change in the variable over time is analyzed to relate the change in the variable to a mass change associated poisoning or inhibiting of the catalyst of first element D1.

Once the measurement(s) of the second mode is/are completed, the temperature of first element D1 may be further decreased to a fifth temperature (which may be below the temperature at which joule heating occurs) so that first element D1 may be operated as a compensating element in a third mode, which is a measuring mode in which the second element D2 functions as a sensing element. Subsequently, in a fourth mode or comparison mode, the temperature of first element D1 may be increased to a sixth temperature (which, as described above, may be above the temperature at which joule heating occurs). Alternatively, the fifth and sixth temperatures may, for example, be ambient temperature or another temperature associated with a power input below which resistance change/Joule heating occurs in the second element. In the third mode, the temperature of second element D2 is increased to a seventh temperature which is above the temperature at which the second catalyst of second element D2 catalyzes combustion of the analyte gas. In the fourth mode, the temperature of second element D2 is decreased to an eighth temperature which is below the temperature at which the second catalyst of second element D2 catalyzes combustion of the analyte gas but above the temperature at which joule heating occurs. The electronic circuitry hereof measures a variable in the fourth mode related to a mass of second element D1. The variable is measured over multiple occurrences of the fourth mode and change in the variable over time is analyzed to relate the change in the variable to a mass change associated poisoning or inhibiting of the catalyst of second element D2. In a number of embodiments, a sensor hereof is repeatedly cycled through the modes described above.

Figure 6B:
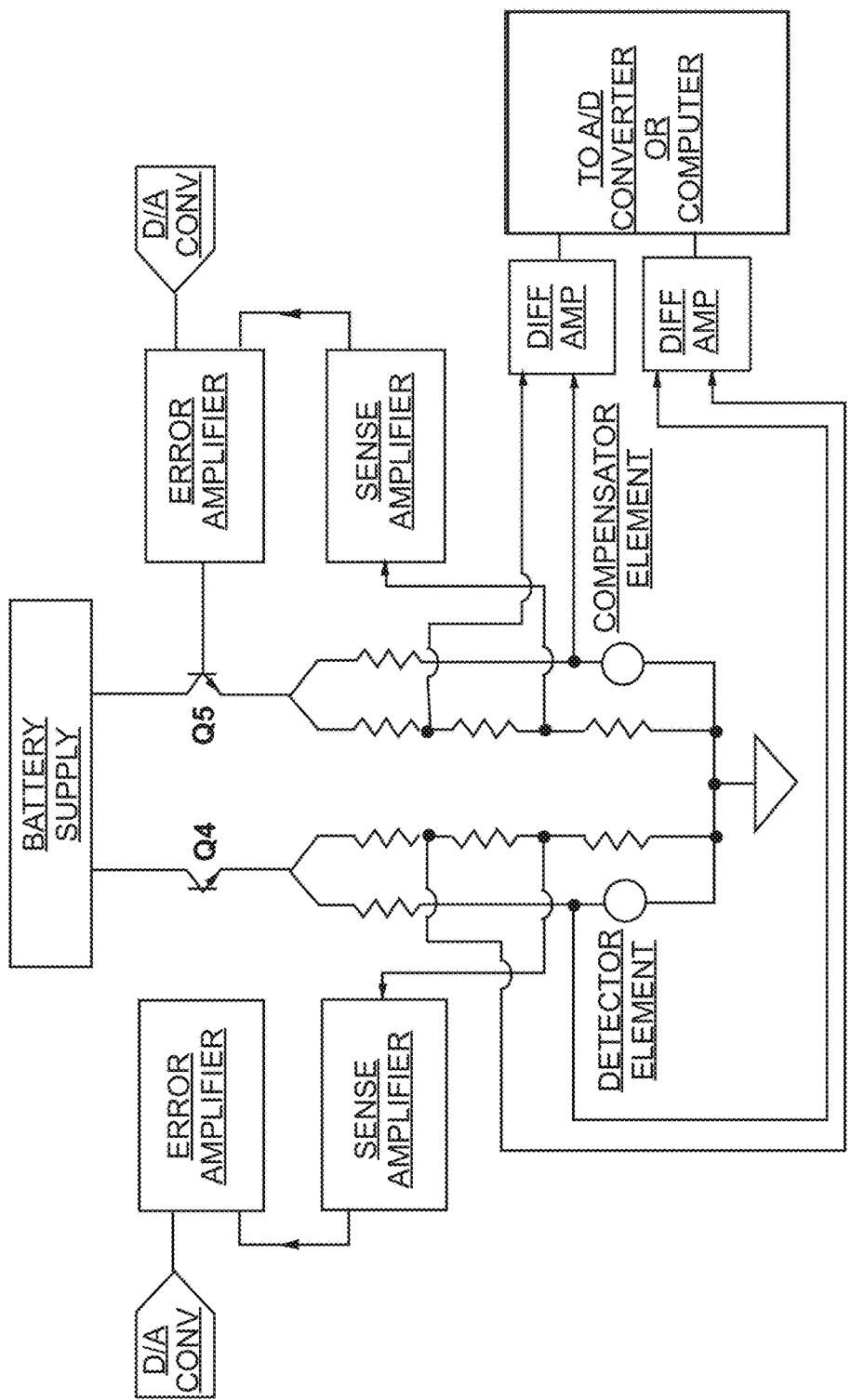
FIG. 6B illustrates another embodiment of electronic circuitry hereof for independent control of multiple elements (that is, sensing elements and compensating elements).

Various electronic circuits and/or control methodologies may be used in the devices, systems and/or methods hereof. As, for example, disclosed in U.S. Pat. Nos. 8,826,721 and 5,780,715, the disclosures of which are incorporated herein by reference, elements or detectors may operate independently (see FIG. 6B for a representative example). As described in, for example, U.S. Pat. No. 5,780,715, FIG. 6B illustrates an embodiment of separate control of detectors/elements in simplified block form. In the illustrated embodiment, the electronic circuit includes two controlled current source circuits, enabled by transistors Q4 and Q5, respectively. Each of transistors Q4 and Q5 may, for example, be a bipolar transistor, a junction field effect transistor, a metal-semiconductor field effect transistor, or a metal-oxide semiconductor field effect transistor. One current source Q4 passes current from the power/battery supply(ies) through the resistive sensor or detector element which is used to detect a combustible gas analyte as describe herein. The other current source Q5 passes current from power/battery supply(ies) through the resistive reference or compensating sensor or element. Current sources Q4 and Q5 may, for example, be controlled by a conventional programmable digital to analog converter (DAC), which may, for example, set the voltage levels at the bases of the enabling transistors Q4 and Q5 to control the amount of current flowing from the power/battery supply(ies) through detector/compensator elements, respectively. In the absence of the combustible gas analyte to be detected, the current through the detector element may be regulated to equal the current through the compensator element. Alternately, the circuitry can be arranged in a controlled voltage source configuration in which a constant identical voltage is ideally maintained across the sensor element and the compensator element.

FIG. 7 illustrates the result of testing a 450 μm diameter catalytic structure using the electronic circuitry of FIG. 6A. Each data point represents data recorded after each 30 second exposure to 15 ppm HMDS. During this recording period, a measurement is taken in both first/measure and second/compare modes. The gas detection mode signal is used to calculate the amount of Span Loss (signal) as compared to the start of the experiment. The compare mode signal is used to calculate the bridge shift as a result of the mass increase on the sensing element or detector. As illustrated in FIG. 7, there is a correlation between the measurements.

In analyzing element response/data hereof to determine if a contaminant such as an inhibitor or a poison has been deposited upon an element hereof, a baseline response may first be established. The baseline response may be established when there is high confidence that the element or elements have not been contaminated. For example, a baseline response may be determined at the time of manufacture. A sensor system may subsequently be placed in a compare or interrogations mode as described above to determine if contamination has occurred. In that regard, one or more thresholds may be established for change in response to determine if poisoning/inhibition has occurred. Such interrogations may, for example, occur periodically. In a number of embodiments, the control system of the sensor system may automatically initiate such an interrogation mode on a periodic or other basis. Moreover, an interrogation mode may also be initiated manually in a number of embodiments.

As described above, element hereof may be relatively small, which reduces the effects of changes in relative humidity and/or pressure in the ambient environment upon element response. Moreover, low thermal time constants associated with low thermal mass assist in providing quick response times and reducing the time an element may be unavailable for use in a gas detection mode. In a number of embodiments, the first sensing element has a thermal time constant of 8 second or less or 6 seconds or less. A sensing or other element may, for example, comprise a MEMS pellistor or a pelement of low thermal mass to provide a thermal time constant of 8 seconds or less (or 6 seconds or less). The thermal time constant of an element is defined as the time required to change 63.2% of the total difference between its initial and final temperature when subjected to a step function change in drive power, under zero power initial conditions.

Although certain advantages may be achieved using element having low volume/low thermal mass as described above, the devices, systems and methods described above may also be used with element of relative high volume/high thermal mass. For example, standard pelements, which may have an effective diameter of greater than or equal to 1 mm may be used herein.

To further illustrate the functionality of the devices, systems and methods hereof, FIG. 8 illustrates the result of a long term application of 15 ppm HMDS to a 450 μm diameter catalytic structure using the electronic circuitry of FIG. 6A. After 25 PPM-HRS of cumulative exposure to HMDS, the device no longer responds to the application of analyte (that is, there is 100% span loss). The second/compare mode signal, however, continues to trend downward. While the sensing element (D2) can no longer respond to the analyte, it can continue to gain mass as the HMDS continues to adhere onto the surface. Therefore, the second/compare mode signal continues to indicate the mass increase.

In several embodiments, pulse width modulation may, for example, be used to control the energy delivered to elements hereof. Pulse width modulation is a well-known control technique used to control the average power and/or energy delivered to a load. In embodiments hereof, a voltage is supplied to, for example, a pellistor element, MEMS hotplate or other heating element to heat a supported catalyst to a desired temperature. Because the elements (including, for example, pelements, pellistors and MEMS elements) hereof may have relatively low thermal mass, the cycle times can be relatively short. Low mass pelements are, for example, described in U.S. Pat. No. 8,826,721 and in U.S. patent application Ser. No. 15/343,956, the disclosure of which is incorporate herein by reference.

As used herein, the term "MEMS pellistor" or "MEMS element" refers to a sensor component with dimensions less than 1 mm that is manufactured via microfabrication techniques. In a number of representative embodiments, sensing elements formed as MEMS pellistors hereof may be manufactured with a thick film catalyst, powered to an operating temperature by resistive heating and are used to detect combustible gases. In a number of representative embodiments, the thickness and diameter for a MEMS catalyst film is 15 microns and 650 microns, respectively.

In pulse width modulation, heating energy (that is, heating voltage(s) or heating currents(s)) may be periodically supplied to the heating element(s) during an "ON time". Rest energy (that is, rest voltage(s) or rest current(s)), which is less than the heating energy may be supplied during a "REST time". The total of the higher-energy or ON time plus the lower-energy or REST time correspond to a cycle time or a cycle duration. Gas concentration or the analyte is measured during the ON time. The heating energy (voltages/currents) supplied during the ON time may be constant during the ON time or may be varied (for example, supplied as heating voltage/current plateau or as heating voltage/current ramp). The rest energy (voltages/currents) may be equal to zero, or be sufficiently lower than the heating energy so that the gas sensor does not consume any gas or substantially any gas to be detected. Similar to the ON time, the rest energy supplied during the REST time may be constant during all the REST time or may be varied (for example, supplied as rest voltage/current plateau or as rest voltage/current ramp). The cycle may be repeated.

An advantage to operating in pulse mode is significantly lower power consumption as compared to continuous mode. Another advantage is improved span response as a result of adsorption of excess combustible gas on the catalyst at cooler temperatures during unpowered or lower powered operation (that is, during the REST time) as compared to continuously powering the catalyst at the run temperature of, for example, 350-600° C.

One may also use a variety of dynamic, pulsed, or modulated operations in a number of embodiment of the interrogation methodologies and systems hereof. In a "dynamic-mode" or "dynamic interrogation mode" operation hereof, an element is briefly energized or de-energized via a change in the electric current flowing therethrough. The length of time of such dynamic interrogation pulses or changes is preferably minimized to decrease the time a sensing element is unavailable to detect analyte. Once again, the elements hereof (for example, MEMS pellistors or pelements) have a low thermal mass as described above. During an individual energy change or pulse, an element hereof experiences transitions through different thermal states. In a number of embodiments hereof, an interrogation method is based on the observation of the non-linear electrical response in the electronic circuitry, hereof of which a catalyst structure and the catalyst supported thereon is a part, as the non-linear thermodynamic action in the catalyst structure transitions from one thermal state to another. A catalyst structure that has become contaminated with poisons or inhibitors will exhibit a measurably different electrical response to a change in energy supplied thereto because of the different thermal properties of the catalyst structure resulting from the contamination. In a number of embodiments, interrogations are based on the measurement of dynamic action of a thermally transitioning catalyst/support structure system and its associated electrical signals, which stands in contrast to other interrogation methods rooted in static analysis of steady-state signals. A dynamic interrogation pulse (in which applied energy is increased or decreased over a short period of time) may be applied to a sensor that is otherwise operating in a continuous mode, wherein energy/temperature is maintained relative constant in one or more modes thereof, or in pulse-mode or pulse width modulation operation as described above. Like other interrogations methods hereof, dynamic interrogation measurements hereof may be carried out in the ambient atmosphere (for example, air) without the application of a calibration gas, test gas or other gas.

In the case of dynamic mode interrogation, it is preferred that the element have a relatively low thermal time constant to, for example, decrease or minimize the length of the dynamic mode interrogation. As described above, the first sensing element may have a thermal constant of 8 second or less or 6 seconds or less.

As described above, in dynamic- or pulse-mode interrogations hereof, the element operating as the compensating element may remain at a temperature below the temperature at which inhibitors and/or poisons deposit/oxidize on the catalyst/catalyst support structure assembly or system. For example, the temperature of the compensating element may be maintained below 150° C. or below 90° C. The compensating element may, for example, receive no energy input and may be maintained at ambient or near ambient temperature. If the compensating element does receive energy input (for example, a pulse of energy contemporaneously with the interrogation pulse of energy applied to the sensing element), the energy input may be maintained below a level which would cause the temperature of the compensating element to rise above the temperature at which inhibitors and/or poisons deposit/oxidize on the catalyst/catalyst support structure assembly or system.

The nature of the stimulus or interrogation pulse of energy, from an electrical standpoint, may be a step function or a controlled ramp or curve from one level to another and (optionally) back again in either direction applied to one or more catalyst structure in one or more circuits simultaneously. The purpose of the pulse or brief energy change is to cause the changes in the thermodynamic properties of the catalyst/support structure system (arising from mass changes associated with contamination) to be revealed as it heats or cools. Because the catalyst structure is part of sensitive electronic circuitry, for example, including a Wheatstone bridge or other bridge configuration, the electrical properties of the electronic circuitry are changed in ways that are measurably different depending on the thermodynamic response of the catalyst structure(s) to the stimulus pulse. These differences can then be analyzed leading to determinations that can be made about the physical condition of the catalyst structure.

Figure 1C:
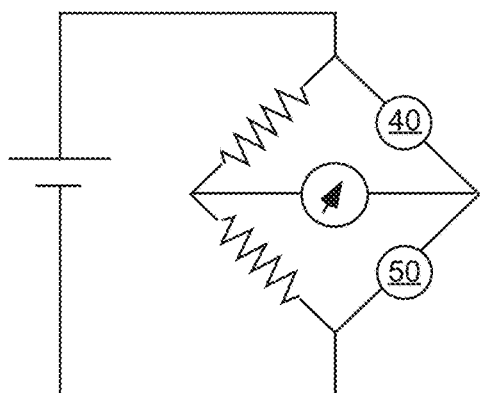
FIG. 1C illustrates an embodiment of the circuitry of the combustible gas sensor of FIG. 1A.
Figure 9A:
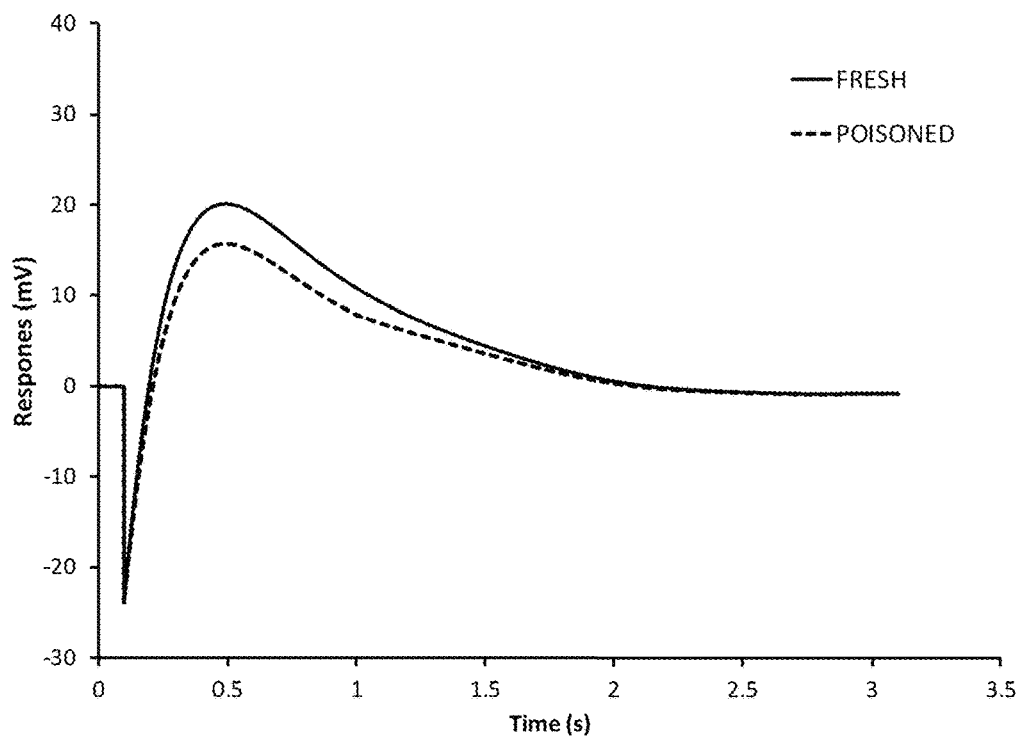
FIG. 9A illustrates the response of an element hereof to an energy pulse (in which energy is increased) for a new sensor including a sensing pelement with a sensitivity of 75 mV in 2.5 volume percent methane in air, and the same sensor after it has been poisoned to a point where it no longer responds to methane in air (that is, the sensitivity is less than 1 mV in 2.5 volume percent methane in air for the studied embodiment).

In dynamic measurements hereof, the circuit containing the catalyst structure may be topologically fixed or other circuits may be switched in or out to obtain the desired measurements. FIG. 9A shows a typical pulse waveform obtained when a Wheatstone bridge circuit including a sensing element and a compensating element (see, for example, FIG. 1C and FIG. 6A) is pulsed with a brief pulse of energy. The shape of the response is the result of the bridge's response to the non-linear changes in the resistance of the elements. Over the duration of the energy pulse, the elements are changing from one thermal state to another as described above. The elements do not necessarily change at the same rate at the same point in time during the changing thermodynamic phases of the event. The resistance in each element changes (perturbing the balance of the bridge circuit) in step with the non-linear thermal changes in the heating element and the catalyst/support structure system. The resulting non-linear change in the measure variable (for example, voltage) may be referred to as an interrogation pulse which can be analyzed electronically or mathematically. In addition to various bridge and other circuits, the sensing element and compensating element may be driven separately as, for example, discussed in connection with FIG. 6B.

Figure 9B:
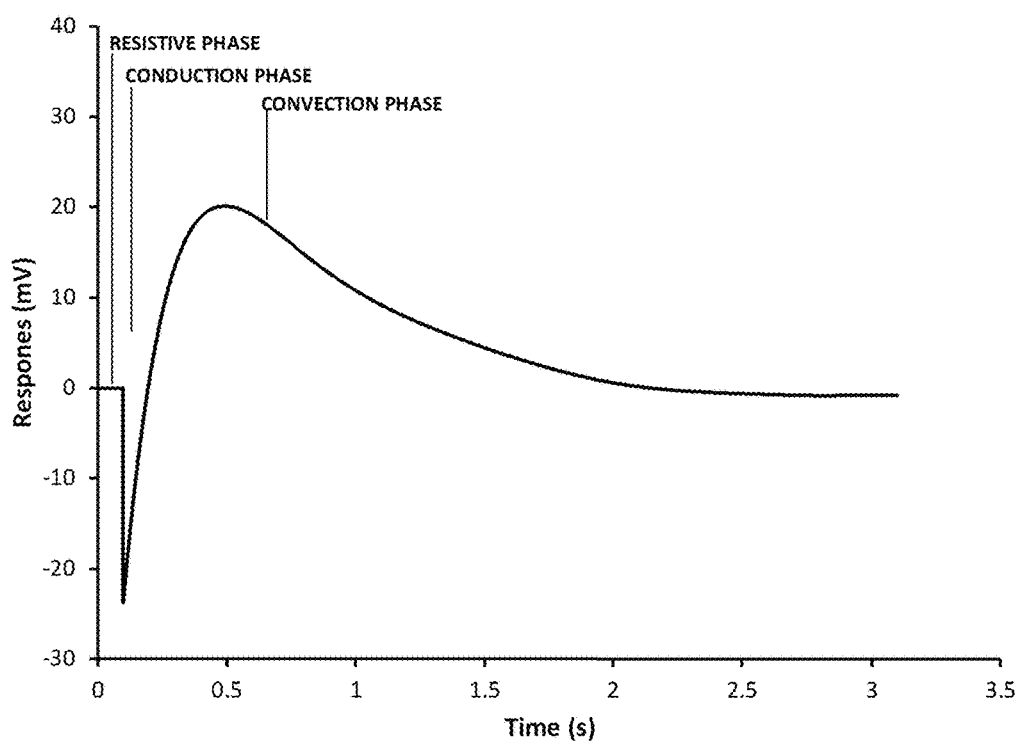
FIG. 9B illustrates the response of the element FIG. 9A to an energy pulse (in which energy is increased) showing various stages of the response.

As illustrated, for example, in FIG. 9B, elements hereof may transition through three phases during an energy pulse. As discussed above, an element may undergo at least three distinct heating effects. FIG. 9B illustrates an energy pulse in which the element begins in a relatively low-energy state (for example, at ambient temperature or a temperature below which joule heating of the heating element occurs) and the applied pulse of energy causes dynamic heating of the element. One skilled in the art will appreciate that similar information can be obtained from an element that is initially at a high temperature state (for example, at a temperature at or above which catalytic combustion of an analyte occurs) and energy is removed from the element to cause dynamic cooling of the element to a lower temperature (for example, to a temperature below the temperature at which joule heating occurs or to ambient temperature). During joule or resistive heating as illustrated in FIG. 9B, passage of an electric current through conductive heating element releases heat, which may be referred to as a resistive phase. During a conductive phase, heat from the heating element transfers from the heating element to the catalyst support structure and the catalyst supported thereon (conduction or conductive heating). Heat transfer then occurs via fluidic convection (convection or convective heating) through the surrounding gases. Eventually, a thermal equilibrium will be reached. Once again, thermal equilibrium will be reached and remain balanced until (a) the ambient temperature changes, or (b) the makeup of the surrounding gas mixture is altered, or (c) the transfer of heat between the wire and the mass of the element changes (as a result of a mass or density change), all of which are competing and interacting effects.

Figure 9C:
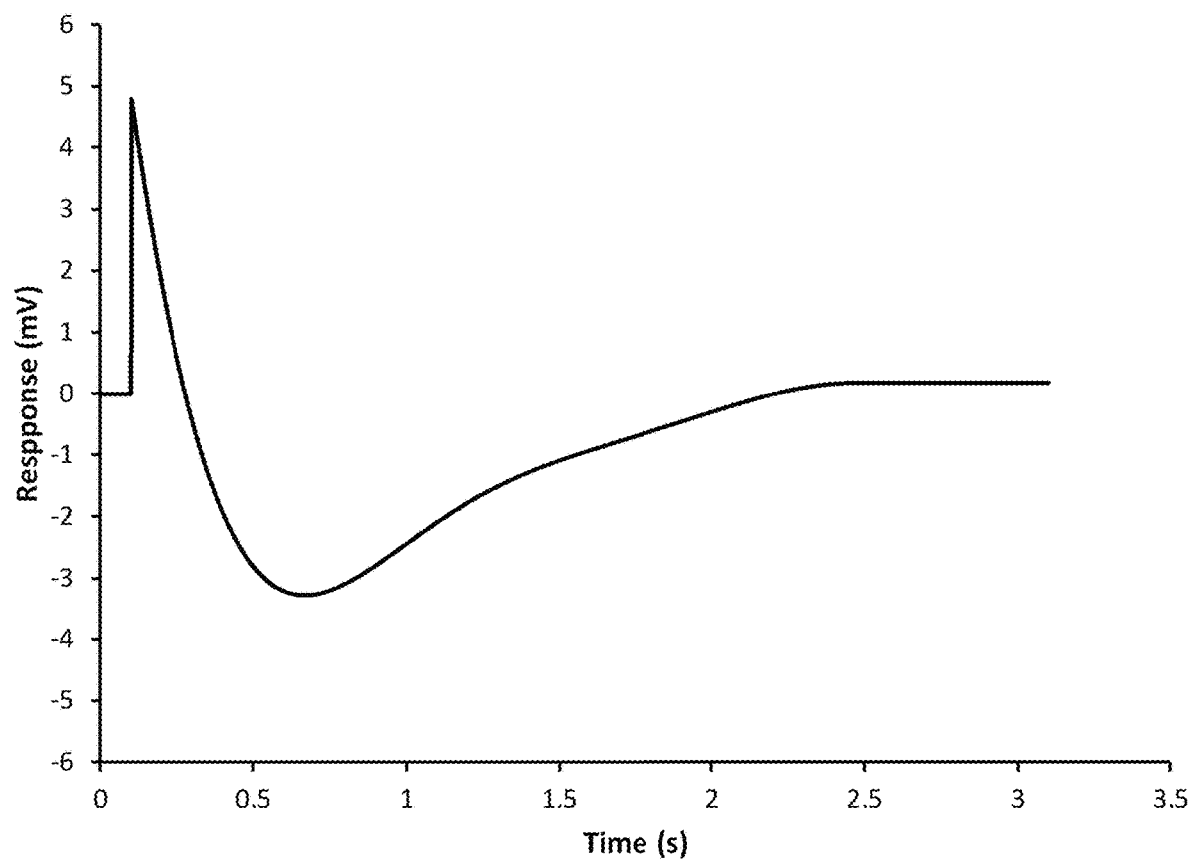
FIG. 9C illustrates the response of an element hereof to an energy pulse in which energy is decreased.

As illustrated in FIG. 9C, a response curve hereof may also be obtained in which energy (and correspondingly temperature) is decreased from a higher energy state to a lower energy state. In such an embodiment, an element may begin in a convective phase and transfer through a conductive phase above until thermal equilibrium is achieved as described above. The decrease in energy may, for example, be of sufficient magnitude and length such that the temperature of the element decreases to a temperature below the temperature at which Joule heating commences.

As describe above, during sensor operation, contamination of the catalyst support structure from poisons and inhibitors changes the mass (and relatedly, the density, effective porosity, effective surface area, and similar physiochemical properties) of the element. These changes are observable in the interrogation pulse that is produced by the instrumented bridge (or other) electronic circuitry.

Figure 10:
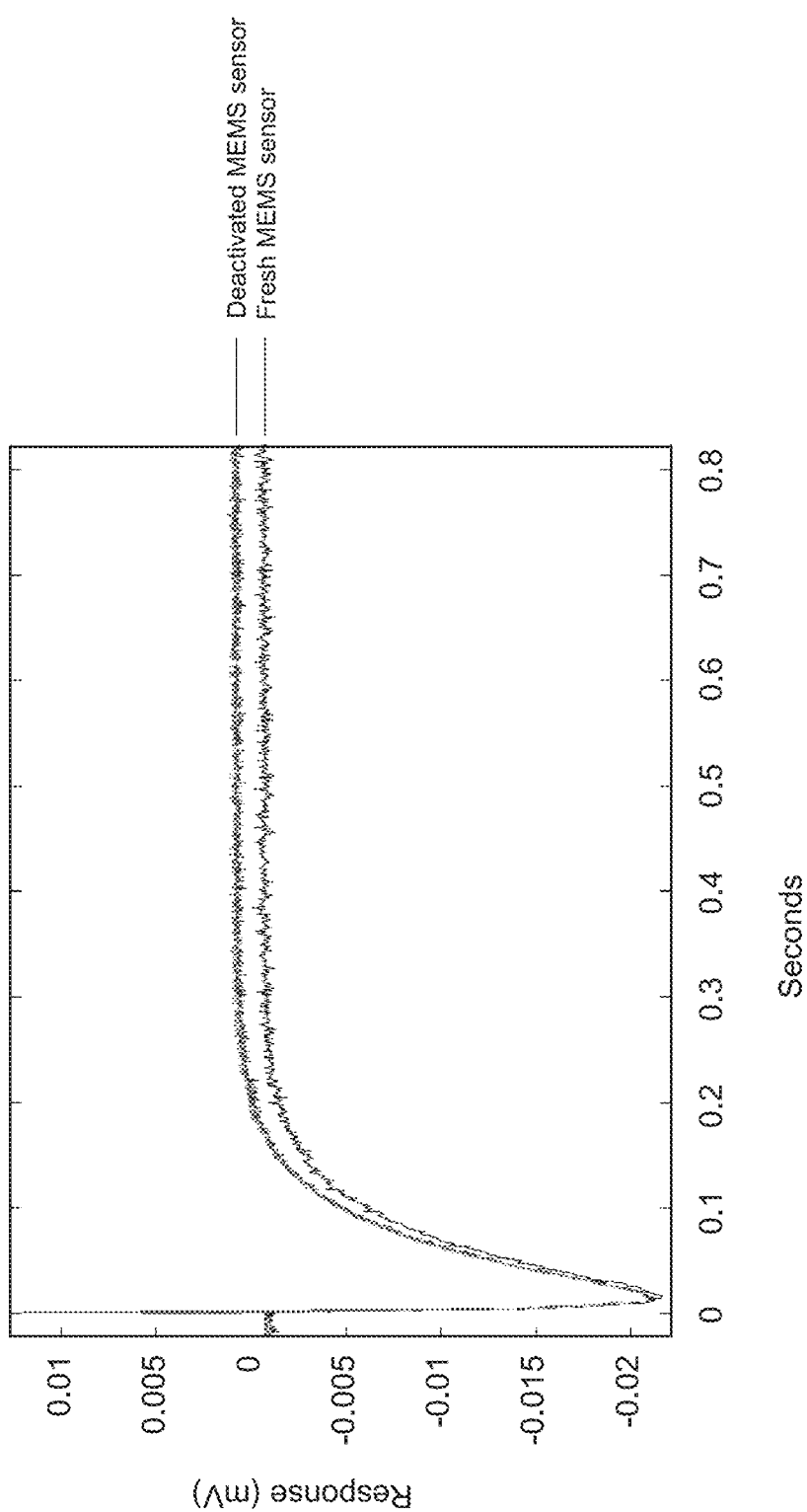
FIG. 10 illustrates the transient response curve of the output from a Wheatstone bridge after a square pulse for a new/fresh sensor, with a sensitivity of 65 mV in 2.5 volume percent methane in air, and for the same sensor after it has been poisoned to a point where it no longer responds to methane in air (that is, the sensitivity is less than 1 mV in 2.5 volume percent methane in air).

The pulses shown in FIG. 9A illustrate the difference in signal between a new sensor including a sensing pelement, with a sensitivity of 75 mV in 2.5 volume percent methane in air, and the same sensor after it has been poisoned to a point where it no longer responds to methane in air (that is, the sensitivity is less than 1 mV in 2.5 volume percent methane in air for the studied embodiment). Similar results may be obtained from catalyst structures deposited on MEMS hotplates. FIG. 10 illustrates the transient response curve of the output from a Wheatstone bridge after a square pulse for a new/fresh sensor, with a sensitivity of 65 mV in 2.5 volume percent methane in air, and the same sensor after it has been poisoned to a point where it no longer responds to methane in air (that is, the sensitivity is less than 1 mV in 2.5 volume percent methane in air for the studied embodiment).

Figure 11A:
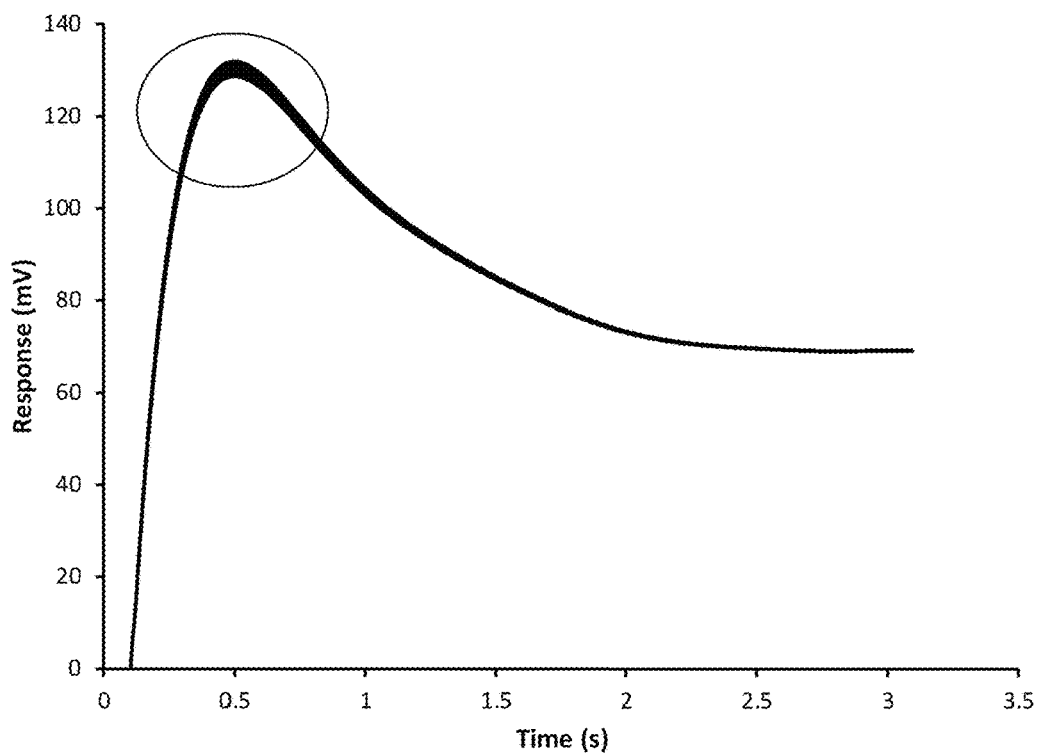
FIG. 11A illustrates a waveform response from a bridge circuit including a sensing element and a compensating element in the form of pelements hereof showing a continued decrease in measure voltage during progressive contamination of the sensing element.
Figure 11B:
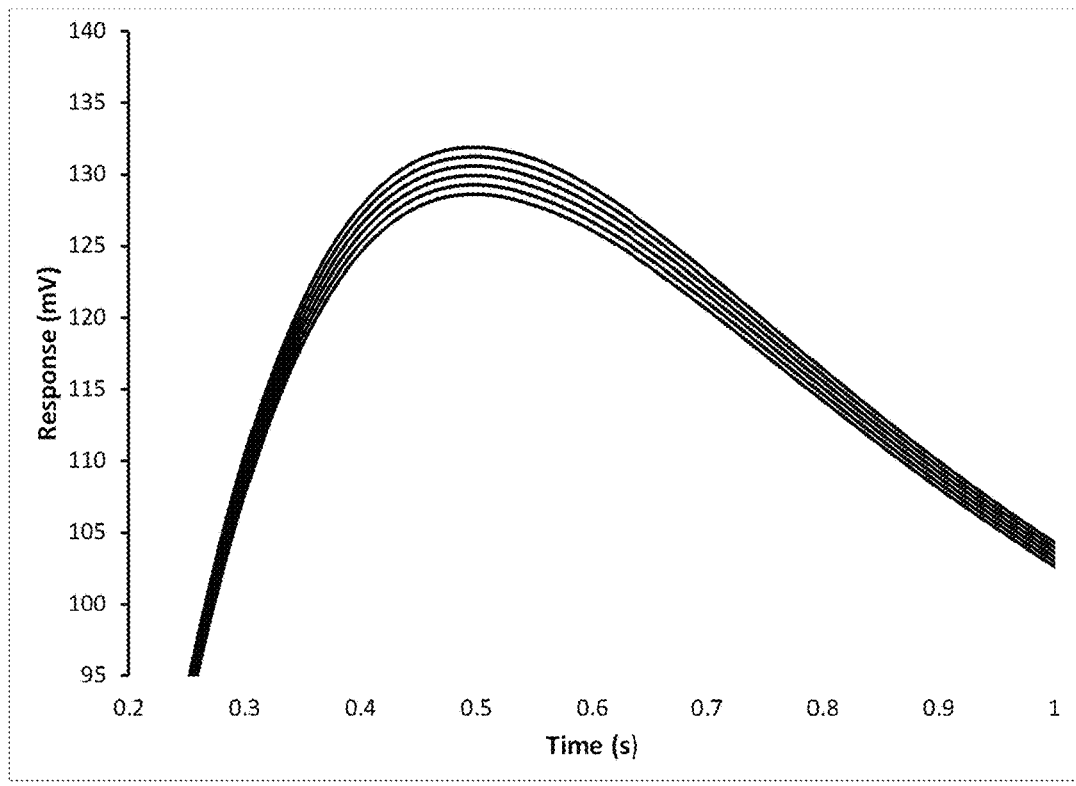
FIG. 11B provides an expanded view of the encircled portion of the graph of FIG. 11A.

Studies hereof have also shown that it is possible to detect the condition of the catalyst/catalyst support structure system at intermediate sensitivity losses so that the gradual loss in performance of the catalyst structure may be measured by the instrument itself (that is, with no requirement of an applied gas(es) such as a test gas or other equipment). The instrument may interrogate its sensor with a stimulus current pulse, capture the electrical response from the bridge circuit and analyze the waveform to make inferences about the condition of the catalyst structure. FIGS. 11A and 11B illustrates a waveform response from a bridge circuit including a sensing element and a compensating element in the form of pelements showing a continued decrease in measure voltage during progressive contamination of the sensing element.

An additional aspect of the pulse interrogation methodology lies in the aforementioned heating phases. All three phases are generally depicted in FIG. 9B. Although many could theorize the relative locations and degree of overlap of each phase, it was found that different information can be obtained from different regions of the response curve set forth in, for example, FIG. 9B. One skilled in the art could further deploy additional methods of applying the power in other time phased forms to further accentuate certain features or regions of the curve. For example, a slow ramp function would allow the resistive phase to occur more slowly. One could then electrically or mathematically evaluate the changes in response to detect changes in the heating element. Furthermore, one could alter the location of the surrounding housing to enhance the convective phase. Many different aspects of the control methodology and systems setup can be considered to optimize the over signal and/or phases thereof.

Additional information may be obtained by examining the response in the different phases of heating as described above. In FIGS. 11A and 11B, the greatest effect from contamination occurred during the peak conductive heating phase with little or no effect in the trailing convective phase. This result indicates that the catalyst structure underwent physical changes in its internal structures. Typically, this occurs when an inhibiting agent reversibly adsorbs onto the catalyst. Sulfur compounds are recognized as one such inhibitor. If an inhibiting adsorbate has been identified, one can use a higher heating period to desorb the element and return the sensing element to its original sensitivity as described further below.

Figure 12:
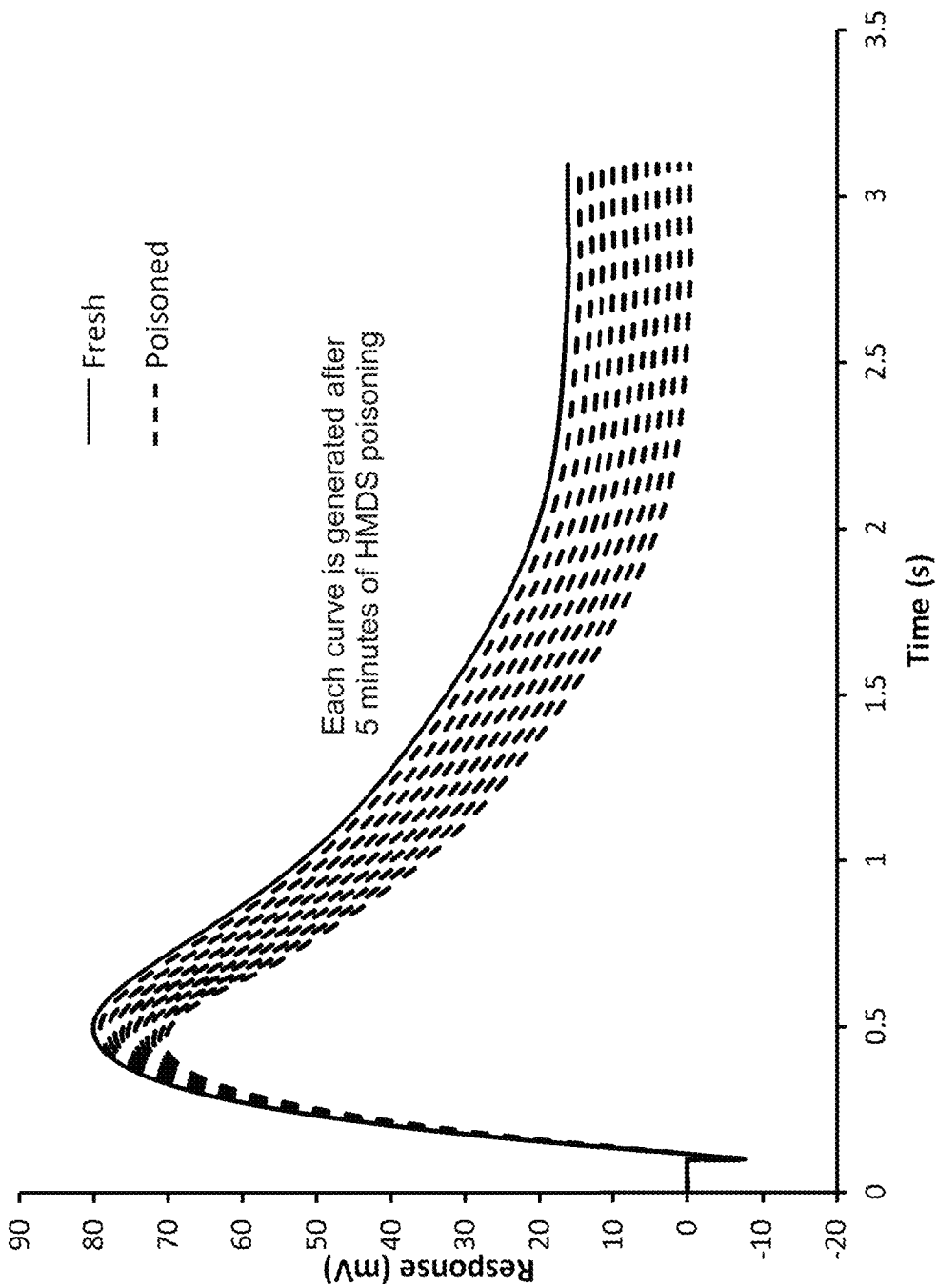
FIG. 12 illustrates change or displacement in a response curve hereof which occurs in a trailing convective phase upon exposure to the common silicone poison HMDS.

Additional consideration may also be given to the convective phases of the interrogation pulses. As illustrated in FIG. 12, significant displacement has occurred in the trailing convective phase when a common silicone poison (HMDS) has been introduced. As the material is oxidized on the outside of the catalyst support structure, the convective heat transfer is changed. As additional poisoning occurs, the change in signal continues to progress and may be represented in many measurable forms. Thus, examining different regions of the response curve to a dynamic energy change may provide additional information regarding the nature of the contamination and determine future actions to be taken.

Similar to described above, a dynamic-mode baseline response may first be established when there is high confidence that the element or elements have not been contaminated (for example, may be determined at the time of manufacture). A sensor system may subsequently be placed in the dynamic-mode interrogation as described above to determine if contamination (poisoning/inhibition) has occurred. One or more threshold values may, for example, be established for slope of the curve, area under the curve, or values at one or more times along the curve. Once again, such interrogations may, for example, occur periodically over time. The control system of the sensor system may automatically initiate such a dynamic-mode interrogation on a periodic or other basis. Moreover, a dynamic-mode interrogation may also be initiated manually.

As also described above, in the embodiment having a first element and a second element wherein each of the first element and the second element includes an active catalyst for catalyzing combustion of the analyte gas, the function of the first element and the second element can be switched. In that regard, in one or more modes of operation, the first element may be operated as a sensing element while the second element is operated as a compensating element. In one or more other modes of operation, the first element may be operated as a compensating element while the second element is operated as a sensing element.

The devices, systems and methods hereof may, for example, be used in connection with other devices, systems and methodologies for detecting poisoning or inhibiting of catalysts (including for example, electronic interrogations methodologies which do not require application of a test or other gas to the sensor). For example, devices, systems and methods disclosed in U.S. Patent Application Publication No. 2014/0273,263, the disclosure of which is incorporated herein by reference) may be used. In such devices, systems and methods, a variable related to the complex component of impedance, which is sometimes referred to as reactance, of the first sensing element (variables that may be measured include, but are not limited to, impedance, reactance, resonant frequency, a frequency dependent variable, inductance, capacitance, or the resistive components of inductance and/or capacitance). Changes in the measured variable over time are used to determine the operational status of the sensing element. Changes in a variable related to reactance are particularly sensitive to contamination of the interior structure of a catalyst support structure and may, for example, be used in conjunction with other systems and methods hereof to assist in determining the existence and nature of any contamination of an element hereof.

Impedance is defined by the formula $Z=R+jX$, wherein Z is the impedance. The real component of impedance Z is the resistance R, while the complex or imaginary component of impedance is the reactance X (wherein j is the imaginary unit). Both capacitive reactance $X_C$ and the inductive reactance $X_L$ contribute to reactance (or total reactance) according to the following formula $X=X_L-X_C$. In general, measurement of impedance or reactance (and/or variables related thereto) requires a variation in applied voltage or current. In the absence of an analyte, resistance of the sensing element remains constant over time, but the complex component of impedance (that is, reactance) varies as a function of sensing element operational state or functionality. Measuring a variable related to reactance may, for example, provide an indication that an inhibitor or poison has entered the catalyst support structure.

In a device, system or method hereof, the measured variable may be used to correct gas concentration output/readings in real-time. Below is a representative example of a formula for adjusting the sensitivity of the system.

$$S_t=S_o*(D_o/D_t*k)$$

In the above equation, $S_t$ is the sensitivity at a given time t; $S_o$ is the initial or previously determined sensitivity, $D_o$ is the initial or previously determined variable related to the dynamic interrogation mode, $D_t$ is the variable measured at a given time t and k is a scaling factor constant. A lookup table may, for example, alternatively be used to related a change in the measured variable to a sensitivity correction.

Furthermore, the measured variable hereof may be used as a trigger to apply additional heat to the catalyst support structure to potentially remove inhibitors. Periodic measurement of the variable, analysis of the results thereof, correction of sensor output and/or application of additional heat may, for example, be effected by control system 300 (via, for example, an algorithm or algorithms stored in memory system 320 as software) in an automated manner without user intervention. The measurement of a variable (for example, voltage, current or resistance) and associated application of additional heat may be done in real time and offer not only a life and health aspect for the system, but a self-curing attribute. Moreover, if the sensor fails to "burn off" a contaminant, it can be determined that the contaminant is a poison. The user may be notified that the active element of the system has been poisoned (for example, via display system 210, alarm system 220 and/or other user interfaces). The "burn off" procedure described herein may, for example, be used in connection with any electronic interrogation of the active sensing element that is suitable to determine that a foreign material has contaminated the active sensing element.

Figure 13:
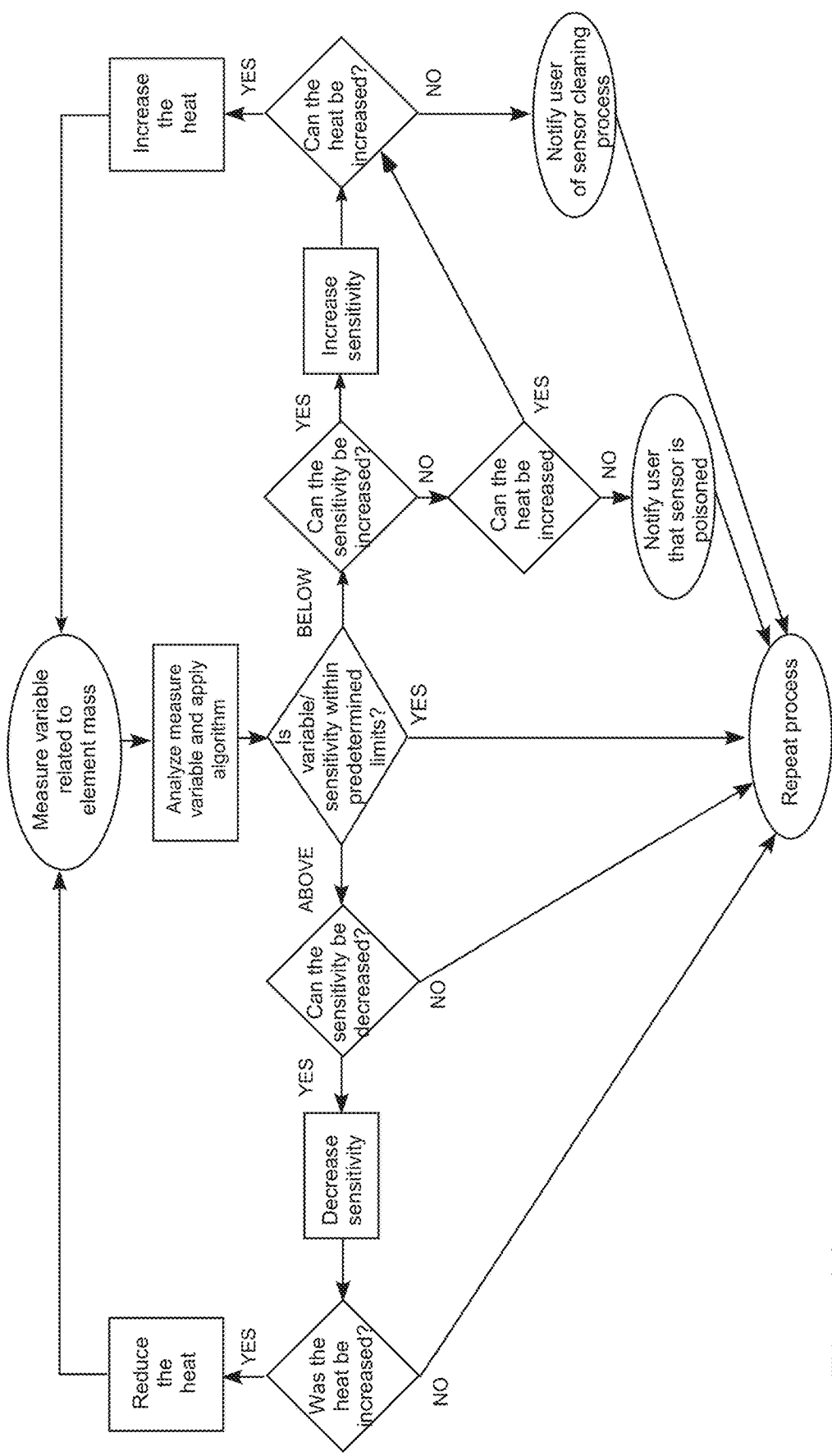
FIG. 13 illustrates a representative embodiment of methodology for operating a sensor hereof.

FIG. 13 illustrates an embodiment of an electronic interrogation or control algorithm or process hereof. In the embodiment of FIG. 13, each time a variable related to mass change in the sensing element is measured, it is evaluated. If the variable and/or a correction of sensitivity associated therewith is within normal limits (for example, +/−1% of a predetermined or threshold value), no corrections occur and the sequence repeats. If a non-conforming result is obtained (that is, the variable and/or correction is not within normal limits), different actions are taken depending upon whether sensitivity should be increased or decreased, which is dependent upon the measured variable. If the measured variable results in a need to increase the sensitivity (for example, associated with contamination of the sensing element), the algorithm will determine if the increase is within normal limits, and do so. If the increase is within normal limits, the system will attempt to increase the heat to burn off any inhibitors, and the user may, for example, be alerted that this "burn-off" or cleaning process is taking place. If the maximum thermal limit has already been applied, and the maximum correction has also been applied, then the user may, for example, be alerted that the sensing element has been poisoned. If the measured variable results in the need to decrease the sensitivity, the algorithm will determine if the decrease is within normal limits, and do so. If the decrease is within normal limits, the system will check to see if heat had been previously applied to attempt to burn off an inhibitor. If heat had been applied, the heat will be reduced. This control algorithm or a similar algorithm hereof may, for example, be an automated procedure carried out via the control system without the need for user intervention. The control algorithm may, for example, be embodied in software stored within memory system 320 and executed by processor(s) 310 of control system 306. In a number of embodiments, the combustible gas sensor is operative to detect the combustible gas analyte during the execution of the electronic interrogation, control algorithm or process.

The devices, systems and/or methods described herein can be used in connection with a variety of types of combustible gas sensors. Existing combustible gas sensors designs are readily modified to include a device or system hereof for measuring an variable related to mass change of one or more sensing elements thereof. For example, such devices, systems and/or methods can be used in connection with Micro-Electro-Mechanical Systems (MEMS), thin/ thick film system, or other suitable micro- or nanotechnology systems such as, for example, described in U.S. Pat. No. 5,599,584 and/or U.S. Pat. No. 6,705,152.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A combustible gas sensor for detecting an analyte gas, comprising: a first element, the first element comprising a first electric heating element, a first support structure on the first electric heating element and a first catalyst supported on the first support structure, the combustible gas sensor further comprising electronic circuitry in electrical connection with the first element, the electronic circuitry being configured to control a level of energy applied to the first element to control the temperature of the first element, the electronic circuitry being configured to heat the first element to at least a first temperature at which the first catalyst catalyzes combustion of the analyte gas and to determine if the analyte gas is present based on a response of the first element being heated to at least the first temperature, the electronic circuitry further being configured to initiate an interrogation of the first element during which energy applied to the first element via the electronic circuitry is changed to induce a transition in a thermal state of the first element, the electronic circuitry being configured to analyze an associated dynamic response of the first element during the transition in the thermal state of the first element and to determine from the associated dynamic response if a threshold response associated with poisoning or inhibiting of the first catalyst has occurred, wherein the associated dynamic response is a change in a measured variable selected from a group consisting of current, voltage and resistance.

2. The combustible gas sensor of claim 1 wherein the level of energy applied to the first element is increased during the interrogation such that the temperature of the first element is increased to induce joule heating and for sufficient time to induce convective heat transfer between the first support structure and surrounding gas or wherein the level of energy applied to the first element is decreased during the interrogation such that convective heat transfer between the first support structure and surrounding gas ceases and for sufficient time so that the temperature of the first element decreases below the temperature at which joule heating of the first element occurs.

3. The combustible gas sensor of claim 2 further comprising a second element comprising a second electric heating element and a second support structure on the second electric heating element, the electronic circuitry being in electrical connection with the second element and being configured to operate the second element to compensate for ambient conditions.

4. The combustible gas sensor of claim 3 wherein the electronic circuitry is configured to maintain the temperature of the second element below 150° C.

5. The combustible gas sensor of claim 3 wherein the electronic circuitry is configured to maintain the temperature of the second element below 90° C.

6. The combustible gas sensor of claim 3 wherein the first element has a thermal time constant less than 8 seconds and the second element has a thermal time constant less than 8 seconds.

7. The combustible gas sensor of claim 2 wherein the electronic circuitry is configured to increase the temperature of the first element during the interrogation to induce joule heating and for sufficient time to raise the temperature of the first element to at least the first temperature.

8. The combustible gas sensor of claim 2 wherein the electronic circuitry is configured to decrease energy applied to the first element during the interrogation to decrease the temperature of the first element from at least the first temperature such that convective heat transfer between the first support structure and surrounding gas ceases and for sufficient time so that the temperature of the first element decreases below the temperature at which joule heating of the first element occurs.

9. The combustible gas sensor of claim 1 wherein the electronic circuitry is configured to initiate a plurality of interrogations to the first element over time, each of the plurality of interrogations comprising a change in the level of energy applied to the first element to induce transition in the thermal state of the first element, the electronic circuitry being configured to analyze one or more associated dynamic responses of the first element during transition in the thermal state of the first element and to determine from the one or more associated dynamic responses if the threshold response has occurred in the measured variable.

10. The combustible gas sensor of claim 9 wherein the electronic circuitry is configured to increase the level of energy applied to the first element and thereby increase the temperature of the first element in each of the plurality of interrogations to induce joule heating and for sufficient time to raise the temperature of the first element to at least the first temperature and, if the electronic circuitry determines that the analyte gas is present after the temperature of the first element is raised to at least the first temperature in one of the plurality of interrogations, the electronic circuitry is configured to not associate a dynamic response in the one of the plurality of interrogations with poisoning or inhibiting of the first catalyst.

11. The combustible gas sensor of claim 1 wherein the first element has a thermal time constant less than 8 seconds.

12. The combustible gas sensor of claim 1 wherein the electronic circuitry is configured to determine the associated dynamic response when the first element is at a temperature below the first temperature.

13. A method of operating a combustible gas sensor for detecting an analyte gas, the combustible gas sensor comprising a first element, the first element comprising a first electric heating element, a first support structure on the first electric heating element and a first catalyst supported on the first support structure, and electronic circuitry in electrical connection with the first element, the electronic circuitry being configured to control a level of energy applied to the first element to control the temperature of the first element and to measure a response of the first element, the method comprising: operating the electronic circuitry to provide energy to the first element to heat the first element to at least a first temperature at which the first catalyst catalyzes combustion of the analyte gas and to determine if the analyte gas is present based on a response of the first element being heated to at least the first temperature, operating the electronic circuitry to initiate an interrogation of the first element during which the level of energy applied to the first element via the electronic circuitry is changed to induce a transition in a thermal state of the first element, and analyzing an associated dynamic response of the first element during the transition of the thermal state of the first element to determine if a threshold response associated with poisoning or inhibiting of the first catalyst has occurred, wherein the associated dynamic response is a change in a measured variable selected from a group consisting of current, voltage and resistance.

14. The method of claim 13 wherein energy is increased during the interrogation such that the temperature of the first element is increased to induce joule heating and for sufficient time to induce convective heat transfer between the first support structure and surrounding gas or wherein the energy is decreased during the interrogation such that convective heat transfer between the first support structure and surrounding gas ceases and for sufficient time so that the temperature of the first element decreases below the temperature at which joule heating of the first element occurs.

15. The method of claim 14 wherein the combustible gas sensor further comprises a second element comprising a second electric heating element and a second support structure on the second electric heating element, the electronic circuitry being in electrical connection with the second element and being configured to operate the second element to compensate for ambient conditions.

16. The method of claim 15 wherein the temperature of the second element is maintained below 150° C.

17. The method of claim 15 wherein the temperature of the second element is maintained below 90° C.

18. The method of claim 14 wherein the temperature of the first element is increased via the interrogation to induce joule heating and for sufficient time to raise the temperature of the first element to at least the first temperature.

19. The method of claim 14 wherein energy is decreased during the interrogation to decrease the temperature of the first element from a temperature of at least the first temperature such that convective heat transfer between the first support structure and surrounding gas ceases and for sufficient time so that the temperature of the first element decreases below the temperature at which joule heating of the first element occurs.

20. The method of claim 13 further comprising initiating a plurality of interrogations of the first element over time, each of the plurality of interrogations comprising a change in energy applied to the first element to either increase or decrease energy applied to the first element to induce an associated dynamic response from the first element in which a thermal state of the first element is in transition, and analyzing one or more of the associated dynamic responses during transition of the thermal state of the first element to determine from the one or more associated dynamic responses if the threshold response has occurred in the measured variable.

21. The method of claim 20 wherein the level of energy applied to the first element is increased in each of the plurality of interrogations to increase the temperature of the first element to induce joule heating and for sufficient time to raise the temperature of the first element to at least the first temperature and, if the electronic circuitry determines that the analyte gas is present after the temperature of the first element is increased to at least the first temperature in at least one of the plurality of interrogations, the dynamic response in the at least one of the plurality of interrogations is not associated with poisoning or inhibiting of the first catalyst by the electronic circuitry.

22. The method of claim 13 wherein the associated dynamic response is determined when the first element is at a temperature below the first temperature.

23. A combustible gas sensor for detecting an analyte gas, comprising: a first element, the first element comprising a first electric heating element, a first support structure on the first electric heating element and a first catalyst supported on the first support structure, a second element comprising a second electric heating element and a second support structure on the second electric heating element, the combustible gas sensor further comprising electronic circuitry in electrical connection with the first element and the second element, the electronic circuitry being configured to control a level of energy applied to the first electric heating element and the second electric heating element to control the temperature of the first element and the second element, the electronic circuitry further being configured, in a first mode, to provide energy to the first electric heating element to heat the first element to at least a first temperature at which the first catalyst catalyzes combustion of the analyte gas and to determine if the analyte gas is present based on a response of the first element to being heated to at least the first temperature, the electronic circuitry further being configured in a second mode to initiate an interrogation of the first element, the interrogation comprising a change in the level of energy applied to the first electric heating element to induce a transition in a thermal state of the first element, the electronic circuitry further being configured to analyze an associated dynamic response during the transition in the thermal state of the first element and to determine from the associated dynamic response if a threshold response associated with poisoning or inhibiting of the first catalyst has occurred, wherein the associated dynamic response is a change in a measured variable selected from a group consisting of current, voltage and resistance.

24. The combustible gas sensor of claim 23 wherein the electronic circuitry is configured to maintain the temperature of the second element below 150° C.

25. The combustible gas sensor of claim 23 wherein the electronic circuitry is configured to maintain the temperature of the second element below 90° C.

26. The combustible gas sensor of claim 23 wherein the electronic circuitry is configured to determine the associated dynamic response when the first element is at a temperature below the first temperature.

* * * * *

UNITED STATES PATENT AND TRADEMARK OFFICE
CERTIFICATE OF CORRECTION

PATENT NO. : 10,948,469 B2
APPLICATION NO. : 15/597859
DATED : March 16, 2021
INVENTOR(S) : Mark Flori Zanella, Sr. et al.

It is certified that error appears in the above-identified patent and that said Letters Patent is hereby corrected as shown below:

In the Specification
Column 10, Lines 58, 59 and 65 delete "support element 150" and insert --support element 160--.
Column 11, Line 59 delete "coil section 120" and insert --coiled section 142--.
Column 24, Line 22 delete "display system 210" and insert --display system 330--.
Column 24, Line 22 delete "alarm system 220" and insert --alarm system 340--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*